US007800059B2

(12) United States Patent
Sato et al.

(10) Patent No.: US 7,800,059 B2
(45) Date of Patent: Sep. 21, 2010

(54) METHOD OF FORMING A SAMPLE IMAGE AND CHARGED PARTICLE BEAM APPARATUS

(75) Inventors: Mitsugu Sato, Hitachinaka (JP); Atsushi Takane, Mito (JP); Takashi Iizumi, Hitachinaka (JP); Tadashi Otaka, Hitachinaka (JP); Hideo Todokoro, Hinode (JP); Satoru Yamaguchi, Hitachinaka (JP); Kazutaka Nimura, Nagoya (JP)

(73) Assignee: Hitachi High-Technologies Corporation, Tokyo (JP)

( * ) Notice: Subject to any disclaimer, the term of this patent is extended or adjusted under 35 U.S.C. 154(b) by 80 days.

(21) Appl. No.: 12/073,359

(22) Filed: Mar. 4, 2008

(65) Prior Publication Data

US 2008/0217535 A1 Sep. 11, 2008

Related U.S. Application Data

(63) Continuation of application No. 11/501,229, filed on Aug. 9, 2006, now Pat. No. 7,361,894, which is a continuation of application No. 10/359,236, filed on Feb. 6, 2003, now Pat. No. 7,164,126, which is a continuation of application No. 10/239,062, filed as application No. PCT/JP01/10168 on Nov. 21, 2001, now Pat. No. 7,034,296.

(51) Int. Cl.
*G01N 23/22* (2006.01)
*H01J 37/26* (2006.01)
*H01J 37/28* (2006.01)
*G21K 7/00* (2006.01)

(52) U.S. Cl. .................. 250/306; 250/307; 250/310; 250/311; 382/278

(58) Field of Classification Search ............... 250/306, 250/307, 309–311, 396 R, 491.1, 492.2, 492.3; 382/274, 276–279, 284, 151; 355/52, 53, 355/77; 356/399
See application file for complete search history.

(56) References Cited

U.S. PATENT DOCUMENTS 3,670,172 A 6/1972 Golden (Continued)

FOREIGN PATENT DOCUMENTS

JP 61-135034 6/1986

(Continued)

*Primary Examiner*—Bernard E Souw

(57) ABSTRACT

An object of the present invention is to provide a sample image forming method and a charged particle beam apparatus which are suitable for realizing suppressing of the view area displacement with high accuracy while the influence of charging due to irradiation of the charged particle beam is being suppressed.

In order to attain the above object, the present invention provide a method of forming a sample image by scanning a charged particle beam on a sample and forming an image based on secondary signals emitted from the sample, the method comprising the steps of forming a plurality of composite images by superposing a plurality of images obtained by a plurality of scanning times; and forming a further composite image by correcting positional displacements among the plurality of composite images and superposing the plurality of composite images, and a charged particle beam apparatus for realizing the above method.

6 Claims, 16 Drawing Sheets

U.S. PATENT DOCUMENTS

| | | | |
|---|---|---|---|
| 4,096,055 A | 6/1978 | Johnson | |
| 4,769,551 A | 9/1988 | Hamashima et al. | |
| 4,772,847 A | 9/1988 | Todokoro | |
| 4,774,460 A | 9/1988 | Todokoro et al. | |
| 4,775,236 A | 10/1988 | Cohen et al. | |
| 4,907,287 A | 3/1990 | Homma et al. | |
| 5,006,795 A | 4/1991 | Yoshizawa et al. | |
| 5,029,250 A | 7/1991 | Komatsu et al. | |
| 5,221,844 A | 6/1993 | van der Mast et al. | |
| 5,227,203 A | 7/1993 | Kibe et al. | |
| 5,257,203 A | 10/1993 | Riley et al. | |
| 5,388,020 A | 2/1995 | Nakamura et al. | |
| 5,434,026 A | 7/1995 | Takatsu et al. | |
| 5,541,411 A | 7/1996 | Lindquist et al. | |
| 5,604,819 A | 2/1997 | Barnard | |
| 5,666,053 A | 9/1997 | Suzuki et al. | |
| 5,681,112 A | 10/1997 | Kuroda et al. | |
| 5,719,478 A | 2/1998 | Washio et al. | |
| 5,866,905 A | 2/1999 | Kakibayashi et al. | |
| 5,869,833 A | 2/1999 | Richardson et al. | |
| 5,929,439 A | 7/1999 | Todokoro et al. | |
| 5,986,263 A | 11/1999 | Hiroi et al. | |
| 6,051,834 A | 4/2000 | Kakibayashi et al. | |
| 6,067,164 A | 5/2000 | Onoguchi et al. | |
| 6,124,140 A | 9/2000 | Do et al. | |
| 6,128,089 A | 10/2000 | Ausschnitt et al. | |
| 6,184,934 B1 * | 2/2001 | Nishiki | 348/383 |
| 6,211,518 B1 | 4/2001 | Richardson et al. | |
| 6,331,885 B1 | 12/2001 | Nishi | |
| 6,448,555 B1 | 9/2002 | Hosokawa | |
| 6,472,662 B1 | 10/2002 | Archie | |
| 6,538,249 B1 | 3/2003 | Yoshida et al. | |
| 6,750,952 B2 | 6/2004 | Grodnensky et al. | |
| 6,864,493 B2 | 3/2005 | Sato et al. | |
| 7,034,296 B2 * | 4/2006 | Sato et al. | 250/307 |
| 7,109,483 B2 * | 9/2006 | Nakasuji et al. | 250/310 |
| 7,138,629 B2 | 11/2006 | Noji et al. | |
| 7,164,126 B2 * | 1/2007 | Sato et al. | 250/310 |
| 7,214,936 B2 * | 5/2007 | Sato et al. | 250/310 |
| 7,241,993 B2 * | 7/2007 | Nakasuji et al. | 250/310 |
| 7,361,894 B2 * | 4/2008 | Sato et al. | 250/306 |
| 7,411,191 B2 * | 8/2008 | Nakasuji et al. | 250/310 |
| 2008/0217535 A1 * | 9/2008 | Sato et al. | 250/310 |
| 2008/0226360 A1 * | 9/2008 | Sugiyama | 399/301 |

FOREIGN PATENT DOCUMENTS

| | | |
|---|---|---|
| JP | 62-43050 | 2/1987 |
| JP | 5-290787 | 11/1993 |
| JP | 5-343020 | 12/1993 |
| JP | 09-166428 | 6/1997 |
| JP | 363266747 | 11/1998 |
| JP | 2000-77019 | 3/2000 |
| JP | 2000-106121 | 4/2000 |
| JP | 2000-294185 | 10/2000 |
| JP | 2000-340496 | 12/2000 |
| JP | 2001-155674 | 6/2001 |

* cited by examiner

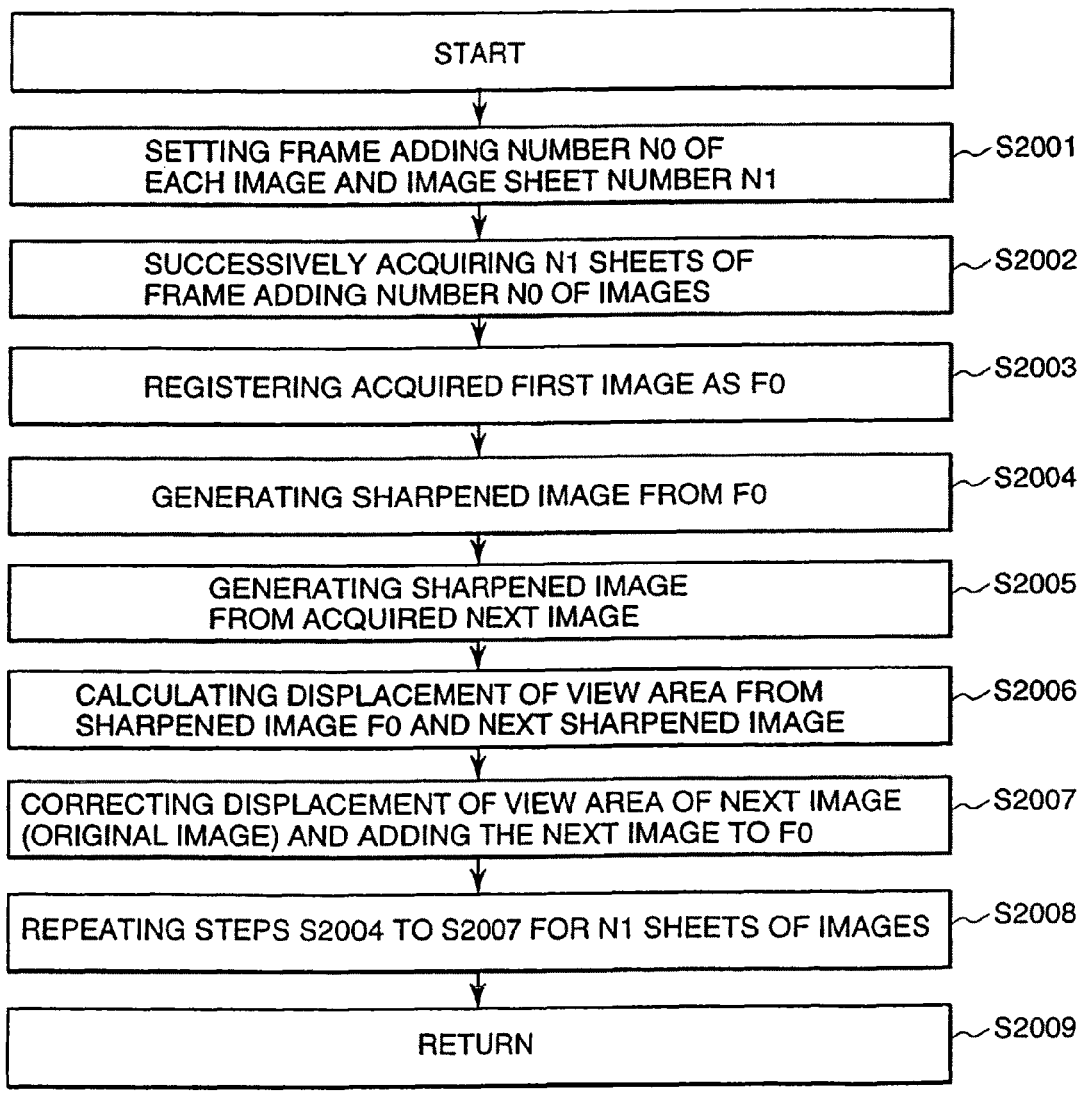

SHARPENING PROCESSING ETC
SHARPENED IMAGES
CALCULATION OF POSITIONAL DISPLACEMENT
POSITIONAL CORRECTION
ADDING PROCESSING

FIG. 7
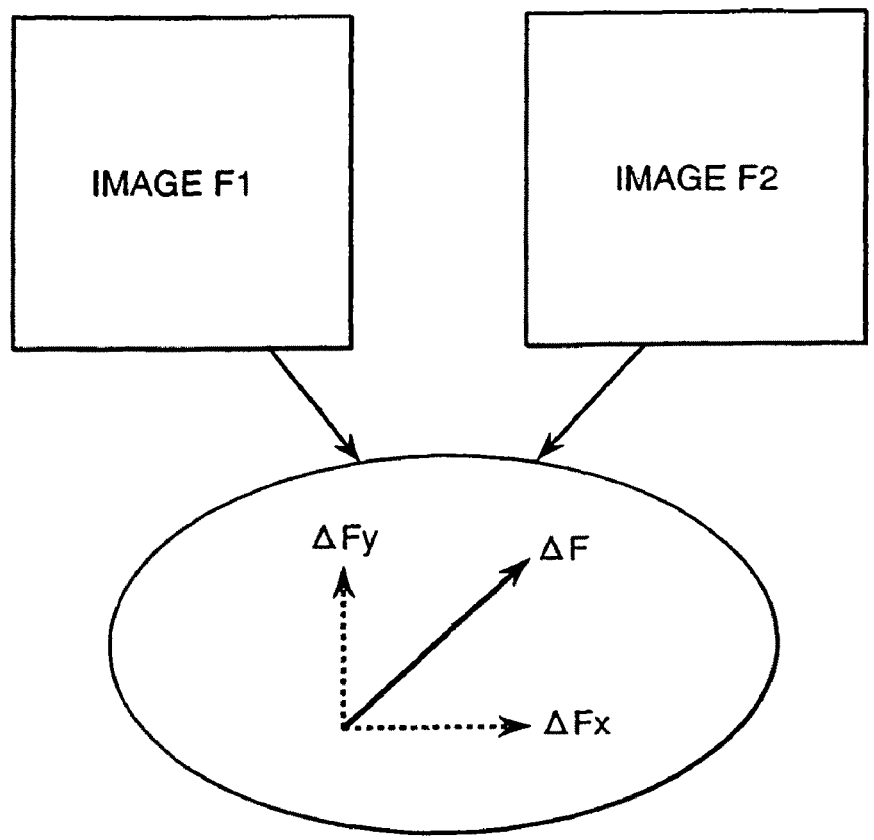
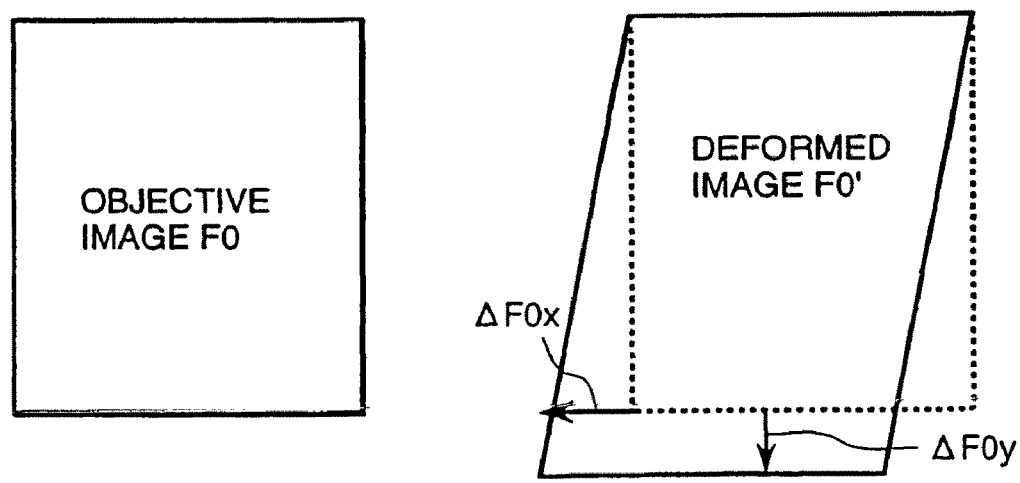

ADDING IMAGES BY CORRECTING
DISPLACEMENT OF VIEW AREA ONLY IN THE
DIRECTIONS SHOWN BY DOTTED-LINE ARROWS

FIG. 14
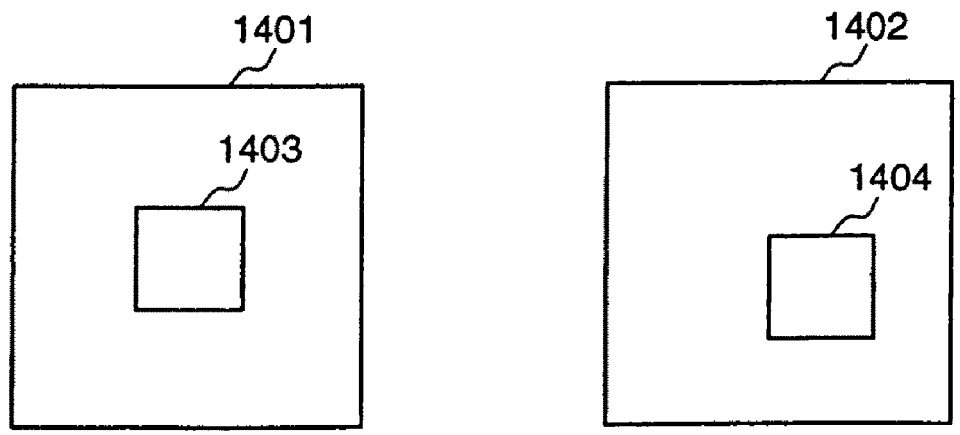
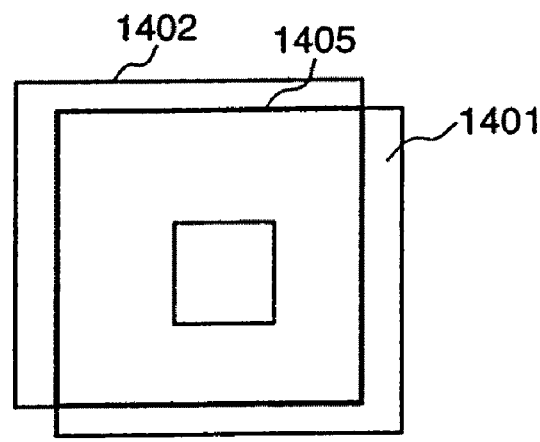
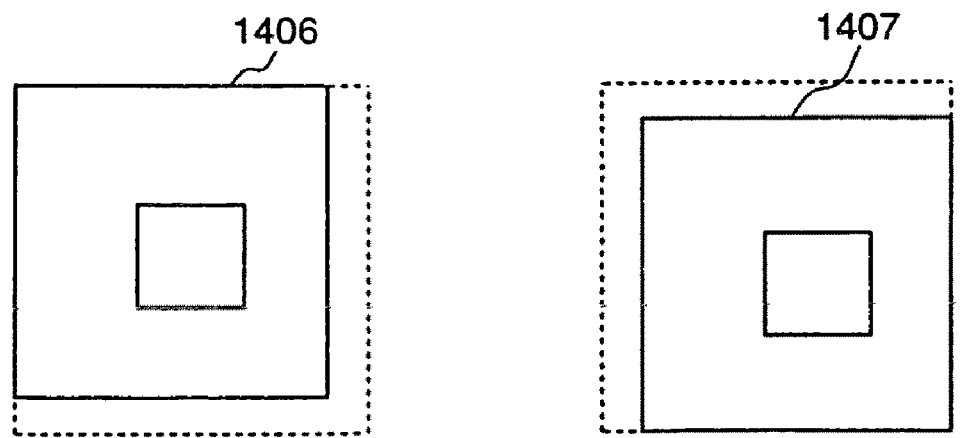

FIG. 15
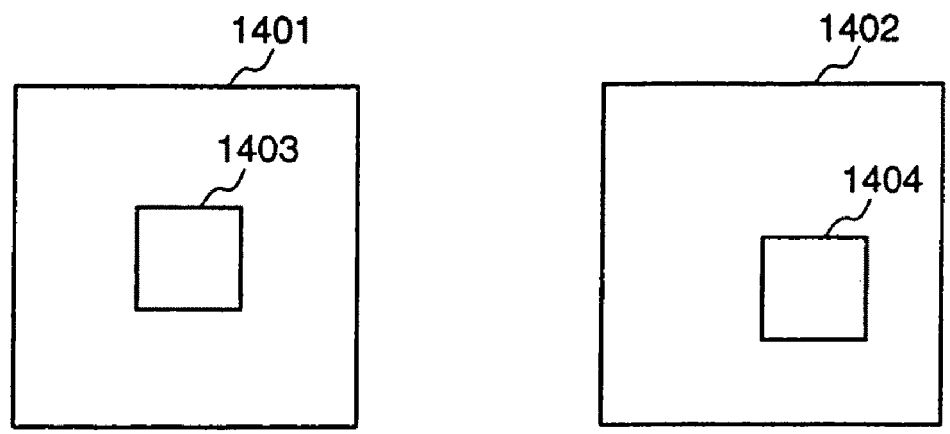
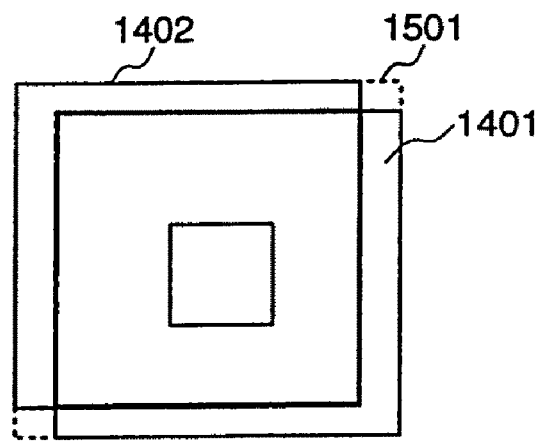
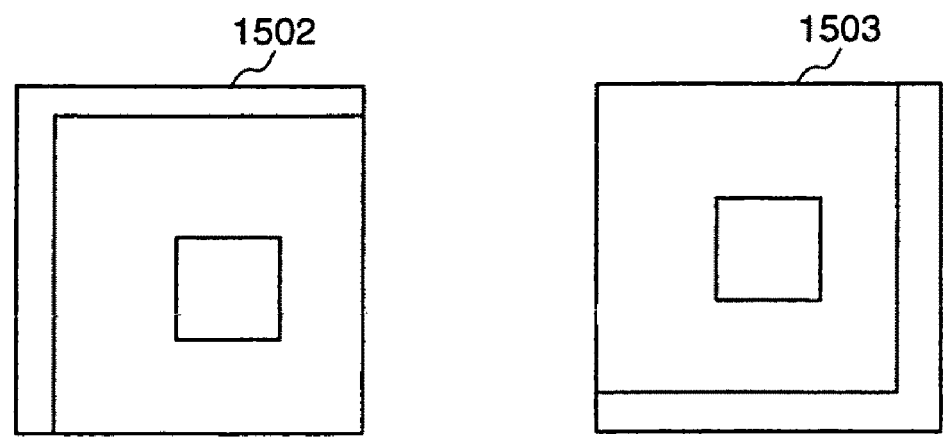

METHOD OF FORMING A SAMPLE IMAGE AND CHARGED PARTICLE BEAM APPARATUS

CROSS-REFERENCE TO RELATED APPLICATION

The present application is a continuation application of U.S. application Ser. No. 11/501,229 filed on Aug. 9, 2006, now U.S. Pat. No. 7,361,894 which in turn is a continuation application of U.S. application Ser. No. 10/359,236 filed on Feb. 6, 2003, now U.S. Pat. No. 7,164,126 which in turn is a continuation application of U.S. application Ser. No. 10/239,062 filed on Oct. 22, 2002, now U.S. Pat. No. 7,034,296 which was the National Stage of International Application No. PCT/JP01/10168, filed Nov. 21, 2001, the disclosures of each of which are incorporated herein by reference in their entirety.

TECHNICAL FIELD

The present invention relates to a method of forming a sample image and a charged particle beam apparatus, and particularly to a method of forming a sample-image and a charged particle beam apparatus which are suitable for obtaining a high resolution image in a high magnification and not influenced by image drift.

BACKGROUND ART

In a charged particle beam apparatus typical of which is a scanning electron microscope, desired information (for example, a sample image) is obtained from a sample by scanning a thinly converged charged particle beam on the sample. In such a charged particle beam apparatus, the resolution becomes higher year by year, and the required observation magnification becomes higher as the resolution becomes higher. As the beam scanning method for obtaining a sample image, there are a method which obtains a final objective image by adding a plurality of images obtained by high speed scanning and a method which obtains a final objective image by once of low speed scanning (acquiring time of one frame image: approximately 40 seconds to 80 seconds). The influence of the drift of a view area on the acquired image becomes more serious as the observation magnification becomes higher. For example, in the method of acquiring the objective image by adding image signals obtained by the high speed scanning pixel by pixel (frame addition), when there is drift caused by charge-up of the sample during adding the images, the objective image after adding has blurs in a direction of the drift because displaced pixels of the view area are added. Reducing the influence of the drift may be attained by reducing number of adding frames and shortening the adding time, but this method can not obtain a sufficient S/N ratio.

On the other hand, in the method of acquiring the image by the low speed scanning, when there is drift during acquiring the image, the image is deformed because the view area flows in a direction of the drift.

A technology is disclosed in Japanese Patent Application Laid-Open No. 62-43050. The technology is that a pattern for detecting drift is stored, and a beam irradiating position is corrected by periodically acquiring an image of the pattern to detect a displacement between the acquired image and the stored pattern.

A technology is disclosed in Japanese Patent Application Laid-Open No. 5-290787. The technology is that two images are acquired based on electron beam scanning on a specified observed area, and pattern matching is performed in order to specify an amount of displacement and a direction of displacement between the both images, and pixels are added by moving the pixels by the specified amount of displacement and the specified direction of displacement.

In the technology disclosed in Japanese Patent Application Laid-Open No. 62-43050, the accuracy of controlling the beam irradiating position becomes insufficient when the observation magnification becomes several hundred thousand times. For example, when an image of 1280×960 pixels is tried to be acquired with an observation magnification of 200 thousand times, the size of one pixel on the observation view area (on the sample) is approximately 0.5 nm. Measurement and evaluation with a higher magnification become necessary as the scale-down of a measured object is progressed. Under such a condition, when the technology is applied to an apparatus for forming a final image by adding a plurality of images, image shift (drift) below several nm causes "blurs" in a flame added image.

Although the technology disclosed in Japanese Patent Application Laid-Open No. 62-43050 suppresses the image shift by controlling the scanning position of the electron beam to correct the drift, the correcting accuracy of the position by such control is limited to several nm to several tens nm. Accordingly, it is almost impossible to correct the position (correct the drift) of an image having a magnification the position above several hundred thousand times with a pixel level. In addition, there is a problem in that the through-put is decreased because stabilization of the drift takes a long time.

On the other hand, the technology disclosed in Japanese Patent Application Laid-Open No. 5-290787 can be appreciated in the point that the position between the images can be corrected in the pixel level, but there is the following problem.

DISCLOSURE OF THE INVENTION

Because an S/N ratio of image data before processing image adding is low and accordingly the displacement between the images is difficult to be detected, it is difficult to correct the displacement with high accuracy. Further, it can be considered that the S/N ratio is improved by increasing the probe current (the electron beam current) to increase the amount of secondary electron emission. However, in a case of an easily charged sample, the displacement between the images acquired at different timing is further increased by movement of the view area of the electron beam due to charging, and as the result, it has been difficult to correct the displacement with high accuracy. Furthermore, in a case where a sample weak against electron beam damage is irradiated by an electron beam having a large beam current, there is a problem in that the sample may be broken or evaporated.

An object of the present invention is to provide a sample image forming method and a charged particle beam apparatus which are suitable for realizing suppressing of the view area displacement with high accuracy while the influence of charging due to irradiation of the charged particle beam is being suppressed.

In order to attain the above object, the present invention provide a method of forming a sample image by scanning a charged particle beam on a sample and forming an image based on secondary signals emitted from the sample, the method comprising the steps of forming a plurality of composite images by superposing a plurality of images obtained by a plurality of scanning times; and forming a further composite image by correcting positional displacements among the plurality of composite images and superposing the plurality of composite images, and a charged particle beam apparatus for realizing the above method.

As described above, since positional displacements can be detected among images having a sufficient S/N ratio without increasing beam current by forming composite images and then correcting the positional displacements, "blurs" of an image at adding the frames can be suppressed because the positional displacements are corrected with high accuracy. The other objects of the present invention and the other detailed construction of the present invention will be described in the section "DESCRIPTION OF THE PREFERRED EMBODIMENTS" in the present specification.

BRIEF DESCRIPTION OF DRAWINGS

FIG. 2 is a flowchart showing the processing of reconstructing an objective image by correcting positional displacements of a plurality of acquired images.

FIG. 7 is a conceptual view showing the process of restoring the deformation of the image acquired by slow scanning, the deformation being caused by the drift.

FIG. 14 is a view explaining a method of detecting the amount of positional displacement and adding the corrected images.

FIG. 15 is a view explaining another method of detecting the amount of positional displacement and adding the corrected images.

DESCRIPTION OF THE PREFERRED EMBODIMENTS

Embodiments of the present invention will be described below, referring to the accompanied drawings.

Figure 1:
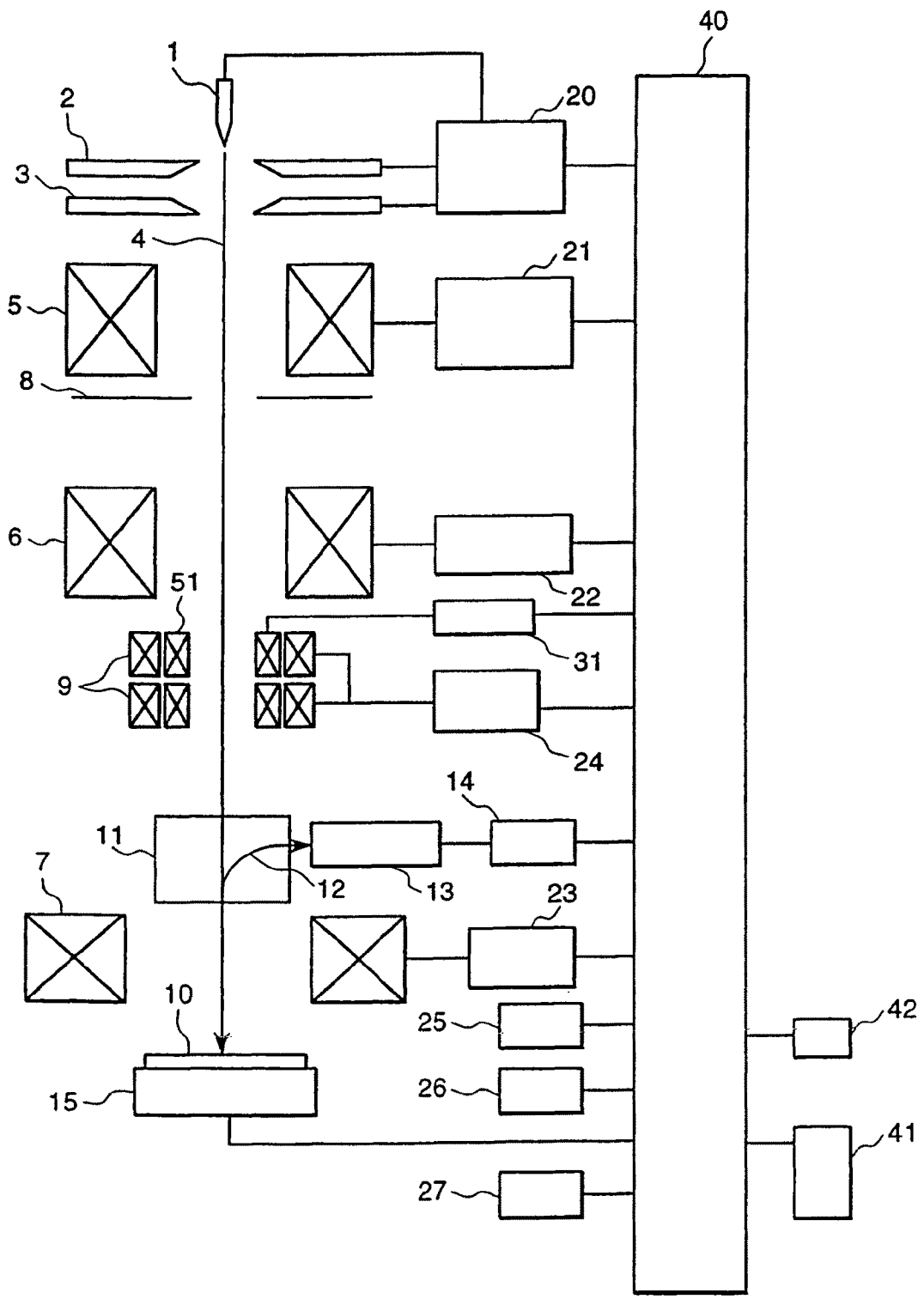
FIG. 1 is a block diagram showing a scanning electron microscope for explaining an embodiment in accordance with the present invention.

FIG. 1 is a block diagram showing an embodiment of a scanning electron microscope in accordance with the present invention. A voltage is applied between a cathode 1 and a first anode 2 by a high voltage control power source 20 controlled by a computer 40 to extract a primary electron beam 4 with a preset emission current from the cathode 1. An acceleration voltage is applied between the cathode 1 and a second anode 3 by the high voltage control power source 20 controlled by the computer 40, and the primary electron beam 1 emitted from the cathode 1 is accelerated and travels to a lens system in the rear stage.

The primary electron beam 4 is focused by a focusing lens 5 controlled by a lens control power source 21. Then, after unnecessary regions of the primary electron beam are removed by an aperture plate 8, the primary electron beam 4 is focused on a sample 10 as a very small spot by a focusing lens 6 controlled by a lens control power source 22 and an objective lens 7 controlled by an objective lens control power source 23. The objective lens 7 may be of various type such as an in-lens type, an out-lens type, a snorkel type (a semi-in-lens type) etc. Further, each of the lenses may be constructed of an electrostatic lens which is composed of a plurality of electrodes.

The primary electron beam 4 is two-dimensionally (in X-Y directions) scanned on the sample 10 by a scanning coil 9. Current is supplied to the scanning coil 9 from a scanning coil control power source. Secondary signals 12 generated from the sample 10 by irradiation of the primary electron beam are travel to the upper portion of the objective lens 7, and then are separated from the primary electrons by a secondary signal separation orthogonally-crossing electro-magnetic field generator 11 to be detected by a secondary signal detector 13. The signals detected by the secondary signal detector 13 are amplified by a signal amplifier 14, and then transmitted to an image memory 25 and displayed on an image display unit 26 as a sample image. The secondary signal detector may be a detector for detecting secondary electrons or reflected electrons, or a detector for detecting light or X-rays.

An address signal corresponding to a memory area of the image memory 25 is generated in a computer 40, and converted to an analogue signal, and than supplied to the scanning coil 9 though the scanning coil control power source 24. The address signal in X-direction is a digital signal repeating, for example, 0 to 512 in a case where the image memory 25 is 512×512 pixels, and the address signal in Y-direction is a digital signal repeating 0 to 512 which is added by 1 when the address signal in X-direction reaches 512 from 0. The signals are converted to the analogue signals.

Since the address of the image memory 25 corresponds to the address of the reflection signal for scanning the primary electron beam, a two-dimensional image of the deflection region of the primary electron beam by the scanning coil 9 is recorded in the image memory 25. The signals in the image memory 25 can be sequentially and successively read out using a read-out address generating circuit (not shown) synchronized by a read-out clock. The signal read-out corresponding to the address is converted to an analogue signal, and becomes a brightness modulated signal for the image display unit 26.

The image memory 25 has a function for superposing (adding) the images (image data items) in order to improve the S/N ratio and then storing the composite image. For example, by superposing images obtained by 8 times of two-dimensional scanning and then storing the composite image, one frame of complete image is formed. That is, a final image is formed by adding images which are formed by once or more times of X-Y scanning. Number of images (number of adding frames) for forming one frame of the complete image may be arbitrarily set, and an appropriate number is set in taking into consideration conditions such as secondary electron generating efficiency and so on. Further, by superposing a plurality of frames each of which is formed by adding the plurality of images, a finally desired image may be formed. By executing blanking of the primary electron beam at the time when a desired number of image frames are stored or after the time, information input to the image memory may be interrupted.

Further, in a case where the number of adding frames is set to 8, it is possible to provide such a sequence that the first frame of image may be deleted when a ninth frame of image is input so that 8 frames of image remain as the result. Otherwise, it is possible to perform weighted addition averaging. That is, when a ninth frame of image is input, an added image stored in the image memory is multiplied by ⅞ and then the ninth frame of image is added to the added image after being multiplied by ⅞.

A two-stage deflecting coil 51 (an image shift deflector) is arranged at apposition the same as that of the scanning coil 9, and thereby, the position of the primary electron beam 4 (the observed area) on the sample 10 can be two-dimensionally controlled. The deflecting coil 51 is controlled by a deflecting coil control power source 31.

A stage 15 can move the sample 10 at least in 2 directions (X-direction and Y-direction) on a plane normal to the primary electron beam.

From an input unit 42, an image acquiring condition (scanning speed, number of adding flames of image) and a method of correcting view area can be specified, and outputting and storing of the images can be also specified.

Further, the embodiment of the apparatus in accordance with the present invention comprises a function for forming a line profile based on detected secondary electrons or detected reflected electrons. The line profile is formed based on an amount of detected electrons when the primary electron beam is one-dimensionally or two-dimensionally scanned or based on brightness information of the sample image, and the obtained line profile is used for dimension measurement of a pattern formed, for example, on a semiconductor wafer. The embodiment of the apparatus in accordance with the present invention may further comprise an interface 41 for transmitting image data to an external unit or the like, and a recording unit 27 for storing image data to an appropriate memory medium.

In the explanation of FIG. 1, the control unit is described as a unit integrated with the scanning electron microscope or the like, but it is, of course, not limited to such a unit. A control processor separately provided from the scanning electron microscope may be used to execute the processing as described below. At that time, a transmitting medium for transmitting signals from the control processor to the scanning electron microscope and input and output terminals for inputting and outputting the transmitted signals through the transmitting medium are necessary.

Further, it is possible that a program for executing the processing to be described below is registered in a memory medium, and the program is executed by the control processor for supplying necessary signals to the scanning electron microscope having an image memory. That is, the embodiments of the present invention to be described below also hold as the invention of program which can be employed to a charged particle beam apparatus such as a scanning electron microscope having an image processor.

Embodiment 1

Figure 5:
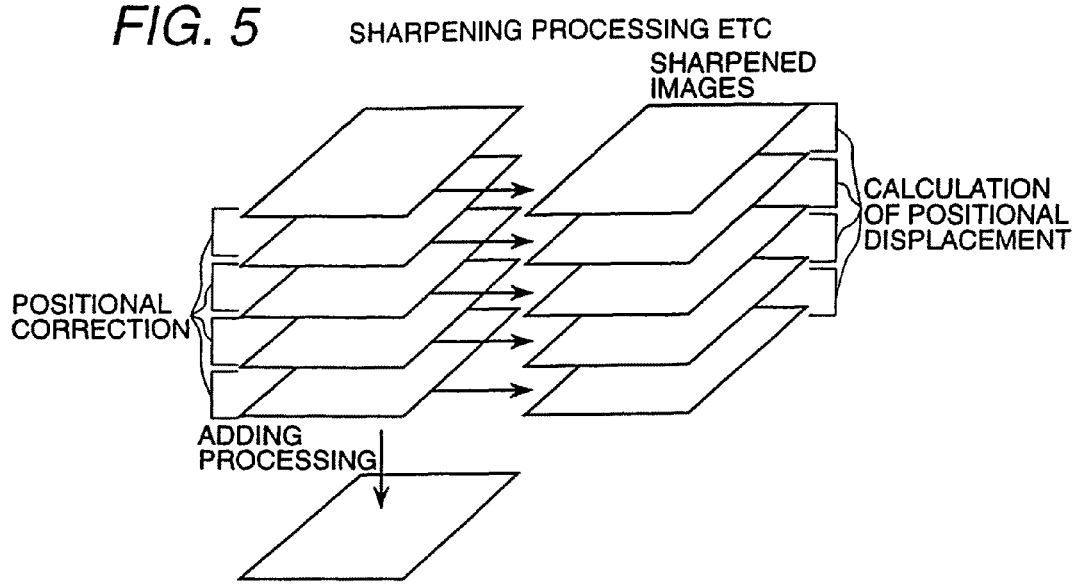
FIG. 5 is a conceptual view showing the process of adding a plurality of images while positional displacements among the plurality of images are being corrected.

In an embodiment of a method of improving an S/N ratio by adding TV scanned images, the processing flow of FIG. 2 will be described below in detail. FIG. 5 is a view schematically showing the processing of FIG. 2.

First Step (S2001):

Number N0 of adding frames for each acquired image and number N1 of acquired image sheets are specified. At that time, total number of adding frames of the final image is N0×N1. In general, by setting the number N0 to 2 frames to 8 frames and the number N1 to 10 sheets to 50 sheets, a necessary S/N ratio can be obtained depending on the purpose. In a case where each of image is acquired with slow scanning slightly slower than the TV scanning, the number N0 may be set to 1 frame. In a case of TV scanning of interlace type, the number N0 can be set to 2. In regard to the condition setting, it is preferable that the plurality of sample images are formed by fixing the optical conditions (a focusing condition of the electron beam and a scanning condition) in order to make detection of positional displacement easy.

Second Step (S2002):

As starting of acquiring image is instructed from the input unit 42, N1 sheets of images of frame adding number N0 (F1, F2, . . . , FN1) in the same view area are successively acquired.

Third Step (S2003):

F1 is set to a memory area of the objective image F0.

Forth Step (S2004):

A sharpened image F0a is produced from the objective image F0. As the sharpening processing, a technique using an image filter for emphasizing edges in the image may be used.

Fifth Step (S2005):

A sharpened image F2a is produced from the image F2.

Sixth Step (S2006):

A positional displacement between the sharpened image F2a of F2 and the sharpened image F0a is detected. Calculation processing such as image correlation may be applied to the detection of the positional displacement.

However, of course, the present invention is not limited to the above, and all the image processing methods capable of detecting the positional displacement are applicable.

Seventh Step (S2007):

Pixels of the original image F2 is shifted by the amount of the displacement of view area detected in the Sixth Step and added to the image of F0, and then the formed image is returned as the objective image F0 again.

Eighth Step (S2008):

By repeating the Fourth Step to the Sixth Step Substituting F3 for F2, the adding processing with the correction of positional displacement is executed to all the N1 sheets of images.

In the present embodiment, the finally obtained image is an image formed by adding N0×N1 frames, but the image is blurred by the drift only when N0 frames are added. Therefore, the blur of the image by the drift is reduced to 1/N1 compared with the case of directly adding N0×N1 frames. By employing such a sequence, it is possible to remove the positional displacement in a direction on the two-dimensional image plane between images acquired at different timing due to charge-up on the sample, and accordingly, image blurs of the image can be suppressed or eliminated.

Figure 3A:
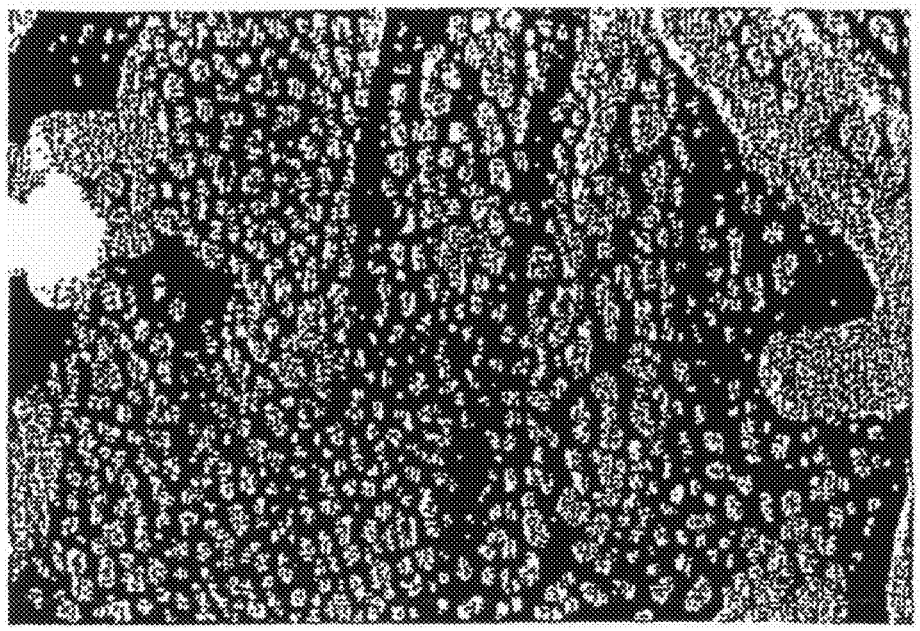
FIG. 3 is photographs showing an image obtained by simply adding images and an image obtained by correcting positional displacements after acquiring a plurality of images and then adding the positional displacement corrected images.
Figure 3B:
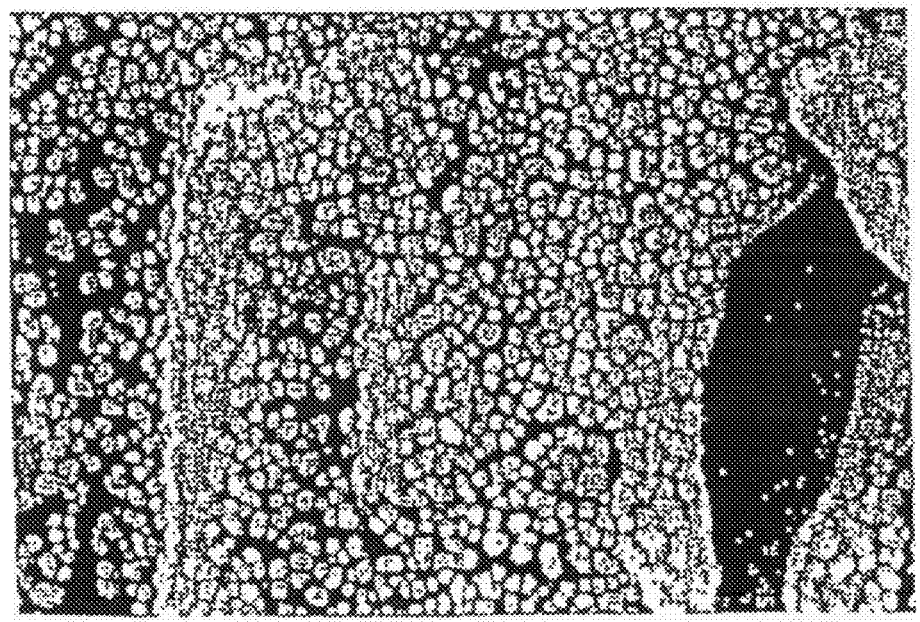

FIG. 3 shows an example of a result obtained by this embodiment. FIG. 3(a) is an image obtained through commonly adding the frames (1280×960 pixels, 200 thousands times of magnification), and drifts are accumulated during adding the images to form conspicuous "blur" in the final image. FIG. 3(b) is an image obtained by acquiring 10 sheets of images having frame adding number 1/10 times as small as the frame adding number of FIG. 3(a), and adding these 10 sheets of the images while the positional displacements are being corrected. In FIG. 3(b), though the total frame adding number of images is the same as that of FIG. 3(a), the "blur" in the final image caused by the drift is also reduced to 1/10 times as small as that in FIG. 3(a) because only the drift accumulated each of the added image becomes "blur" in the final image and the acquiring time for each image is 1/10 times as short as that in FIG. 3(a).

Since the amount of drift changes depending on the kind of the sample, the optical condition and so on, it is preferable that N0 and N1 are set corresponding to the S/N ratio. Since number of scanning times (number of images) required for securing a required S/N ratio is determined based on the quality of obtained image and the efficiency of generating secondary electrons, N0 and N1 may be determined in taking the degree of drift into consideration. Further, it is also possible to construct the sequence that by inputting a parameter expressing conditions of the sample (easiness of charge-up etc) and at least one of total adding number, number of adding frames (N0) and number of acquired images (N1), the other two parameters are determined. According to such a construction, the apparatus condition can be easily set only by inputting specification necessary for observation.

In the present embodiment, although the positional displacement between the frame-added images is corrected, the present invention is not limited to the above. Correction of the positional displacement may be executed by the unit of an arbitrary number of frames or by the unit of arbitrary number of acquired sheets. At that time, unless an image to be compared with for detecting the positional displacement has an S/N ratio larger than a certain value, the drift detecting accuracy will be decreased. Therefore, it is preferable that number of images necessary for securing a desired S/N ratio is set as the frame adding number (N0), and then number of acquired image sheets (N1) for obtaining a necessary S/N ratio for the final sample image is set.

In the present invention, the image may be stored in the image memory 25 after correcting the positional displacement. Otherwise, by preparing a frame memory Corresponding to (frame adding number)×(acquired images), the positional displacement among sample images may be corrected when the sample image is displayed, or when the sample image is transferred to an external image memory element, or before the sample image is transferred to the external image memory element. Otherwise, the positional displacement among sample images may be corrected in the external image memory element.

By preparing at least an image memory for storing a composite image, an image memory for storing images before executing superposing processing and an image memory for storing an image to be acquired, images acquired one after another by the electron beam scanning can be successively superposed.

In the present embodiment, in order to make the setting of N0 and N1 for specified samples easier, the system may be constructed in such that a reference image for each combination of N0 and N1 is stored, and the reference image can be read out at setting N0 and N1. By doing so, an operator can set appropriate N0 and N1 by referring to the reference image.

It is preferable that when drift is fast, number of displacement corrections is increased by decreasing number of frames N0, and that when drift is nor so fast, number of frames N0 is increased in order to improve the quality of the image to be compared with. For example, it is preferable that as a means for appropriately setting numbers of N0 and N1, a means for adjusting N0 and N1 stepwise is provided. In a case where the total adding frame is set to 50, the combinations of N0 and N1 are 1×50, 2×25, 5×10, 10×5, 25×2 and 50×1. However, by providing a means for adjusting the combination and a means for displaying an actually added image, the operator can set appropriate N0 and N1 from the superposed image without detailed knowledge on the technology in regard to the present invention.

By providing the adjusting means described above, not only in the case of correcting the displacement, but also in a case where the quality of image is changed by changing the combination of N0 and N1, an appropriate combination of N0 and N1 can be easily selected.

Further, the same effect can be attained by providing a means for adjusting the degree of displacement correction which sets N1 to a larger value when "the degree of displacement correction is large" is selected, and sets N0 to a smaller value when "the degree of displacement correction is small" is selected.

Embodiment 2

Figure 4:
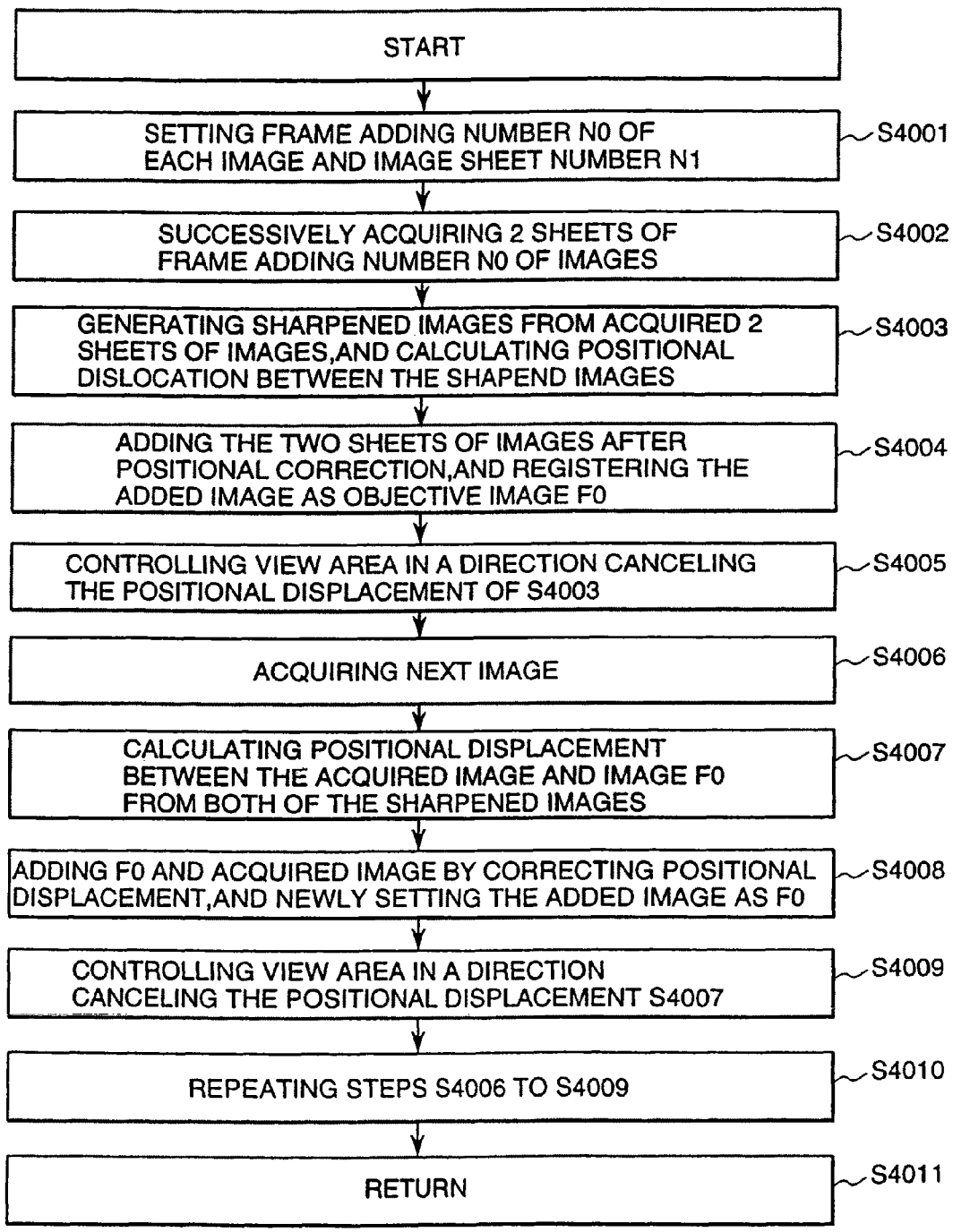
FIG. 4 is a flowchart showing the processing combining of the processing of correcting the drift by controlling the beam irradiating position or the sample position and the processing of correcting the positional displacements of a plurality of acquired images and then adding the plurality of images of which the positional displacements are corrected.

A processing flow of FIG. 4 will be described below in detail.

First Step (S4001):

Number N0 of adding frames for each acquired image and number N1 of acquired image sheets are set.

Two sheets of images of the frame adding number N0 are successively acquired.

Third Step (S4003):

Sharpened images are generated from the acquired two sheets of images, and a positional displacement between the sharpened images is calculated.

Therein, when the amount of this displacement exceeds a preset allowable value, each of the images before correcting the position and being added conspicuously includes "blurs" due to drift. Therefore, the processing is stopped, and a display function may notify the operator that the drift is too large.

Fourth Step (S4004):

The two sheet of images after correcting the positional displacement are added to each other, and the added image is registered as F0.

Fifth Step (S4005):

The view area is moved in a direction canceling the positional displacement obtained in the process of S4003.

Therein, as the shifting means, each of a method of using an electric view-area shifting means (an image shift deflector) and a method of using a stage is available depending on the amount of shifting. In general, when the amount of shifting is small, both of the image shift deflector and the stage are used. When the amount of shifting is large, the stage is used or the image shift deflector is used if necessary. By canceling the displacement of the view area using image shift deflector and the stage, the displacement between the images can be compressed even if there is a comparatively large drift. Therefore, it is possible to solve the problem that an effective view area (an area where view areas of images are overlapped with one another) after correcting the positional displacement by the image processing becomes narrow.

Sixth Step (S4006):
The next image is acquired.

Seventh Step (S4007):
By forming a sharpened image of the acquired image and a sharpened image of F0, a positional displacement between the sharpened images is calculated.

Eighth Step (S4008):
The image F0 and the image acquired in S4006 are added by correcting the positional displacement between the images, and the added image is newly set as F0.

Ninth Step (S4009):
The view area is moved in a direction canceling the positional displacement obtained in the process of S4008.

Tenth Step (S4010):
By repeating the process S4006 to the process S4009, N1 sheets of images are obtained, and the obtained images are added.

According to the above construction, a large drift component can be corrected by the stage and the beam deflection, and very small drift of pixel level can be corrected at adding the images. Therefore, a high resolution image can be obtained by effectively correcting even a comparatively large drift.

On the other hand, in order to minimize the effect of drift, it is necessary to minimize the acquiring time of each of the images for correcting the positional displacements and then being added to the limit. However, the limit is determined by the S/N ratio of the images necessary for detecting the positional displacement. Therefore, if the amount of the drift exceeds a certain value, each of the images itself for detecting the positional displacement becomes blurred due to drift. When an amount of drift causing such a result is detected, a means for displaying that a high resolution image is difficult to be acquired or for stopping the measurement may be provided. By doing so, it is possible to solve a problem of uselessly operating the apparatus under a state that acquiring of the sample images is clearly difficult.

Embodiment 3

Figure 6:
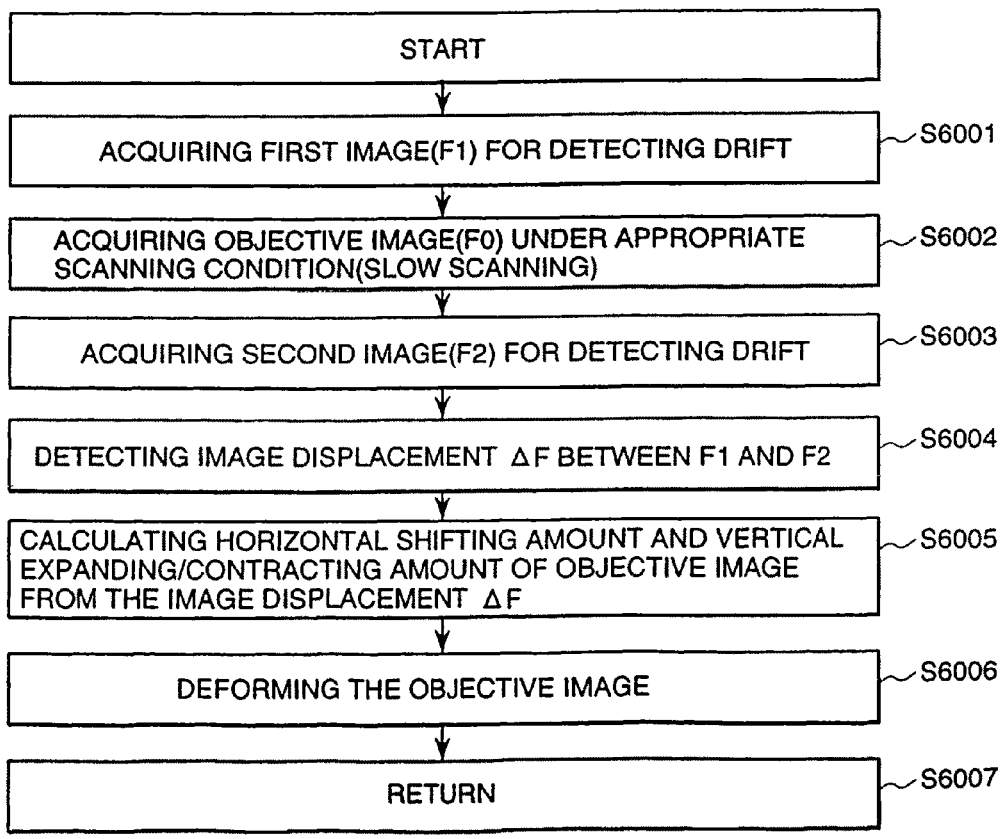
FIG. 6 is a flowchart showing the processing of restoring deformation of an image acquired by slow scanning, the deformation being caused by the drift.

A processing flow of FIG. 6 will be described below in detail.

First Step (S6001):
A first image F1 for detecting drift is acquired.

Second Step (S6002):
An objective image F0 is acquired under an appropriate slow scanning condition. By acquiring the image under such a slow scanning condition, a high contrast image can be obtained because secondary electrons can be generated more compared to the case of fast scanning.

Third Step (S6003):
A second image F2 for detecting drift is acquired.

Fourth Step (S6004):
A displacement ΔF (ΔFx, ΔFy) between the images F1 and F2 is detected.

Fifth Step (S6005):
Amounts of deformations in the horizontal direction and the vertical direction of the objective image are calculated from the amount of image displacement AF.

Sixth Step (S6006):
A new image F0' is formed by deforming the objective image F0.

Here, the processing of Fifth Step will be described below in detail, referring to FIG. 7.

Letting the amount of displacement between the drift detecting images F1 and F2 acquired into the image memory be ΔF (ΔFx, ΔFy), and a time difference between acquiring the image F1 and acquiring the image F2 be ΔT, drift speeds (Vx, Vy) in X-direction and Y-direction can be calculated by the following equations.

$$Vx = \Delta Fx / \Delta T, \quad Vy = \Delta Fy / \Delta T$$

On the other hand, letting an acquiring time of the objective image F0 be T0, a displacement of view area of the image F0 generated during the time period from starting scanning to ending scanning can be expressed as follows.

X-direction $\Delta F0x = Vx \times T0$

Y-direction $\Delta F0y = Vy \times T0$

Therefore, as shown in FIG. 7, by deforming the objective image F0 in the image memory by F0x (Y-direction) and ΔF0y (X-direction) toward the directions of correcting the drift, it is possible to reproduce the estimated image F0' which would be obtained if the drift did not occur.

In the present embodiment, the images F1 and F2 for detecting drift are acquired before and after acquiring the objective image F0, respectively, but, of course, the present invention is not limited to the above. The images F1 and F2 may be successively acquired before acquiring the image F0 or after acquiring the image F0. In that case, the deformation is estimated from the displacement between the images F1 and F2 at the time when the image F0 is acquired, and then the estimated image F0' can be reproduced.

Each of the images F1, F2 and F0 is stored in the image memory, and the images F1 and F2 are read out based on judgment on necessity of image reproduction, and then the reproduction processing is performed.

According to the construction described above, the shape of an observed object deformed by drift can be accurately known.

Particularly, in the case of slow scanning, the electron beam is being irradiated on the sample, and accordingly deformation of the sample image due to charging of the sample becomes large. Therefore, application of the technology of the present embodiment is very effective in slow scanning. Further, although the present embodiment has been described on the case of two images for correcting drift and one image to be corrected, the present invention is not limited to the above and arbitrary number of images may be used.

Figure 16:
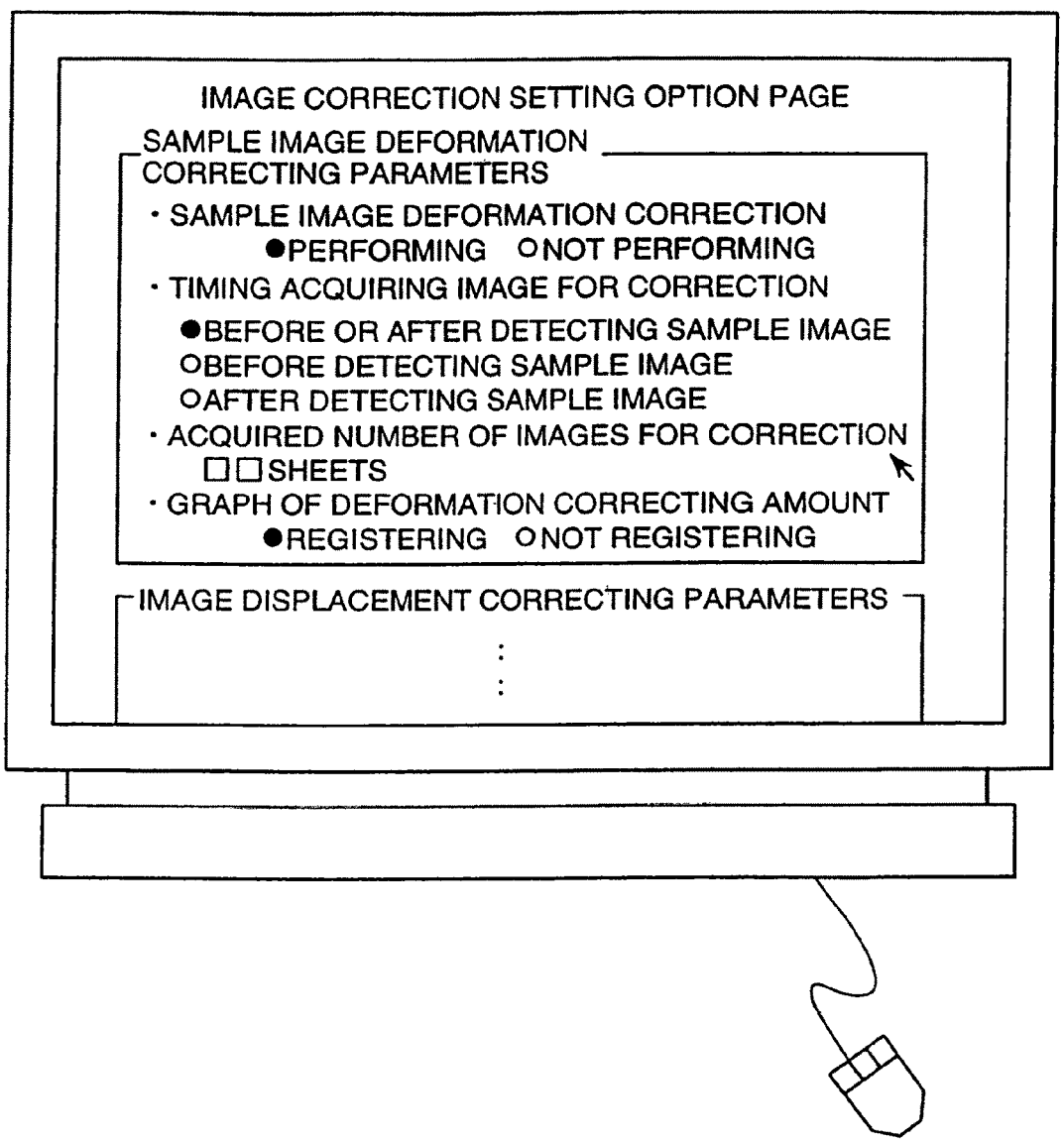
FIG. 16 is a view showing an example of a GUI page displayed on an image displaying unit.

Further, in order that the operator judges the necessity of image reproduction, in the apparatus of the present embodiment, option buttons for selecting necessity of image reproduction are provided on a graphical user interface (GUI), as shown in FIG. 16. Although FIG. 16 shows the example of performing selection using a pointing device or the like on the image display unit, the present invention is not limited to this method. Setting may be performed using another well-known input setting means.

In the observation using an electron beam apparatus such as a scanning electron microscope, there is a need that the sample image is highly accurately formed. On the other hand, there is also a need that damage of the sample is reduced by suppressing irradiation of the electron beam as low as possible. In the case of the embodiment of the apparatus in accordance with the present invention, the sample image can be firmed with high accuracy if the deformation of the sample due to drift can be suppressed, but the electron beam scanning for acquiring at least the images F1 and F2 is further required, which is different from the case of simply forming the image F0. That is, since the scanning time of the electron beam is increased, possibility of the sample damage caused by 7 the electron beam irradiation is increased, By providing the option described above, the operator can select necessity of the reproduction taking a status of the observed object or the condition for forming an appropriate sample image into consideration, and can form the sample image which the operator desires.

Further, by making a graph on what extent the deformation is corrected and registering the graph, the information can be used for setting the scanning speed and for judgment of necessity of drift correction.

Further, by storing and displaying number of scanning times of the electron beam and amount of correction and the amount of deformation versus the irradiation time, it is possible to know the sample image is deformed by how long the electron beam is scanned.

Embodiment 4

Figure 8:
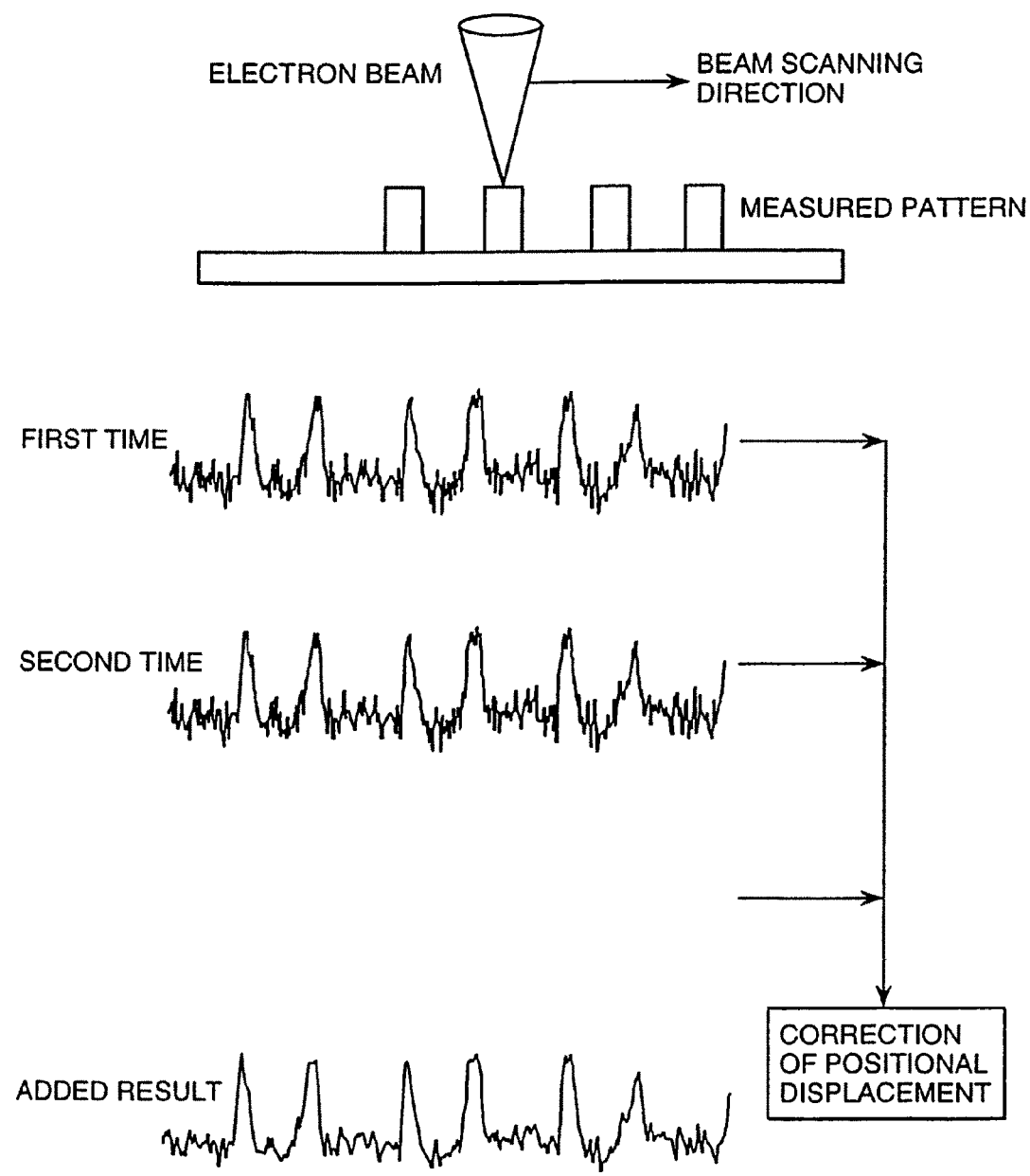
FIG. 8 is a conceptual view showing the process of correcting the positional displacements among a plurality of profiles obtained through line scanning and then adding the plurality of images of which the positional displacements are corrected.

An embodiment of applying the drift correction technology to addition of line profiles will be described below, referring to FIG. 8.

In general, measurement of dimension of a pattern on a wafer uses a signal distribution (a line profile) which is obtained when an electron beam is line-scanned on a pattern of a measured object. In a case where the sample is an insulator, high speed scanning is performed in order to prevent disturbance caused by charging. Therefore, since a signal obtained by once of line scanning is bad in the S/N ratio, it is difficult to perform highly reproducible measurement. Accordingly, in general, signal distributions obtained from several times of scanning are added to form a profile of the measured object. At that time, if drift occurs in the direction of line scanning, the added line profile becomes dull, and accordingly the accuracy of measurement is decreased.

Therefore, each of the profiles obtained by plural times of line scanning is stored, and positional correction of the profiles is performed so that the correlation among the profiles becomes highest, and then the profiles are added. In this case, a signal acquired by once of scanning may be used as each of the profiles before addition. However, when the scanning speed is high, the signal acquired by once of scanning is too bad in the S/N ratio. Therefore, signals obtained by minimum number of scanning times within a range capable of correlating among the profiles are simply added, and the added signal may be used as each of the profiles before addition. By this method, the problem of dullness of the profile is improved even if there is drift, and a profile having a high S/N ratio can be produced. Therefore, it is possible to perform highly reproducible measurement.

Further, the apparatus may be constructed in such that the setting page described in FIG. 16 is also used for selecting the necessity of positional correction. A semiconductor inspection apparatus or the like may be constructed in such that reliability of the measurement can be checked later by sounding an alarm or setting a flag to the measurement when an amount of positional correction exceeds a threshold and clearly increases. Therein, in a case where an amount of correction, a added profiler and profiles before adding are stored, or in a case where the line profile is formed based on a two-dimensional scanned image, the apparatus may be constructed in such that the added image or the images before adding are stored and displayed on an image display unit later.

According to the construction described above, when a measured object is erroneously measured in a repetitive pattern or the like where patterns of the same type are adjacently arranged, the erroneous measurement can be easily checked.

Particularly, in the case where a line profile is formed through one-dimensional scanning, the measurement can be rapidly performed compared to the case of two-dimensional scanning. However, it is impossible to check the accuracy of measurement by referring the sample image. In the present embodiment, the line profile can be formed with high accuracy even in the case of one-dimensional scanning by which the measurement can be rapidly performed. For example, even in an apparatus measuring length of a pattern based on a line profile, the length can be measured with high accuracy based on the line profile formed with high accuracy.

In a case where a pattern width of a line pattern having roughness is measured, the measuring length range is expanded toward directions perpendicular to the direction of measuring length, and measurement of length based in the line profile is performed using a plurality of different positions within the measuring length range. Then, the plurality of obtained measured length values are averaged, or the dispersion values of roughness are measured based on the plurality of measured length values obtained within the expanded measuring length range. The present embodiment is also applicable to this case.

For example, by performing addition of line profile with the above-mentioned positional correction for each of the plurality of the length measuring positions, and then by measuring the average value or the dispersion value of roughness, these resultant values can be obtained with high accuracy.

Even in a case where the line profiles are displaced depending on the length measuring position due to charge-up or the like, the added line profile can be appropriately formed and the length can be accurately measured by performing positional correction, using one reference line profile, to the line profiles in the other positions, not by performing positional correction for each of the plurality of the length measuring positions. According to the construction described above, reliability evaluation of electric property of a semiconductor element pattern can be easily realized regardless of existence of roughness.

Further, in the case of measuring lengths of a plurality of positions, when a measured length value of one of the positions is extremely different from the measured length values of the other of the positions, there is a possibility that a part of the line pattern is extremely thinned, or that a failure of the length measurement occurs. In such a case, the apparatus may be constructed in such that an error message is output or that the measured results such as the sample image and the line profile are registered together with the measuring conditions so as to check the results later by read out the data.

Embodiment 5

Figure 9:
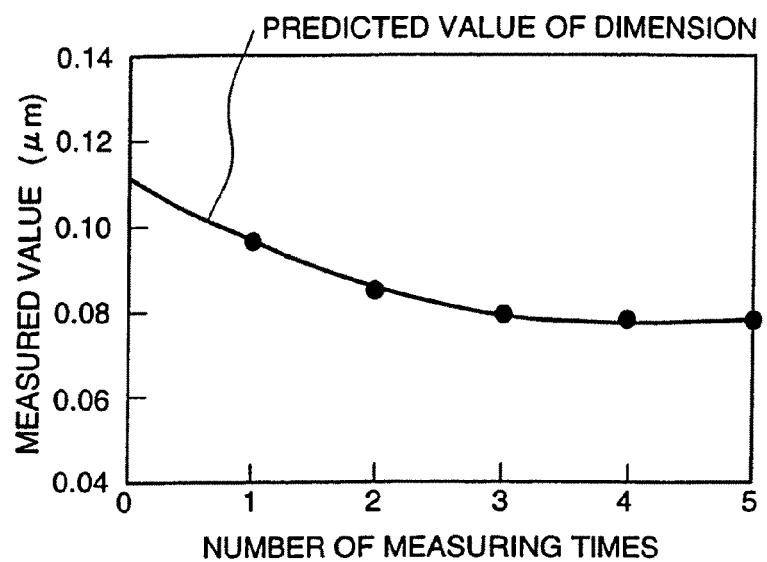
FIG. 9 is a graph showing an example of estimating the beam damage from measured length values in a plurality of acquired images to calculate a measured value of length which is not influenced by beam damage.

FIG. 9 is a graph for explaining an example of estimating an accurate dimension from time-varying pattern dimensions by repeating measurement of the same pattern plural times. The object to be measured using an electron beam is damaged to be shrunk or evaporated depending on the material by irradiation of the electron beam. In such a case, since the pattern dimension is decreased as the amount of beam irradiation increases, the measurement itself is an error cause.

In order to evaluate the correct dimension by estimating the error caused by the measurement itself, the same pattern is measured plural times. Since the amount of beam irradiation is increased in proportion to number of measuring times, deformation of the pattern is also increased as the number of measuring times is increased. Therefore, the pattern dimension before irradiating the beam or before shrinking at starting the beam irradiation can be estimated by obtaining the relationship between the number of measuring times (in proportion to the amount of beam irradiation) and the dimension measured value. In the embodiment of the apparatus in accordance with the present invention, a sequence for automatically executing the above-described dimension estimation is installed.

The apparatus may be constructed in such that in order to Judge later whether or not the dimension estimation is correctly performed, a table graphing number of measuring times versus measured value is stored, and then output to the display unit or an external output unit. For example, in a case where an observed object is shrunk and at the same time drift also occurs, the dimension estimation may be not appropriately performed by influence of the drift, the operator can check by referring to the above-described graph whether or not the dimension estimation is correct. By storing a sample image obtained at that time corresponding to the stored graph, the correctness of the dimension estimation can be checked referring to the sample image.

The apparatus may be constructed in such that when the above-described graph records an abnormal trend, the graph is selectively stored or a preset flag is set. For example, when an abnormal change is observed in a graph expressing the trend of dimension change, something may occur in the electron beam apparatus at that time, and accordingly the dimension measurement may be not correctly performed. If the apparatus is constructed so that the graph or the sample image can be selectively checked at that time, the operator can efficiently check the correctness of the dimension estimation without performing useless check.

Although the abscissa of the graph expresses "number of measuring times" in the present embodiment, the abscissa may express another parameter such as "number of scanning times" or "time". The ordinate is not limited to express "measured value" either, and the ordinate may express a ratio of a measured value to a normal value (a design value).

By forming a dummy pattern having a condition equivalent to a measured object pattern at a position near the measured object pattern when the present embodiment is applied to an apparatus for measuring length of a semiconductor pattern, measurement of length can be accurately performed without shrinking the pattern which affect operation of the semiconductor element.

Embodiment 6

Figure 10:
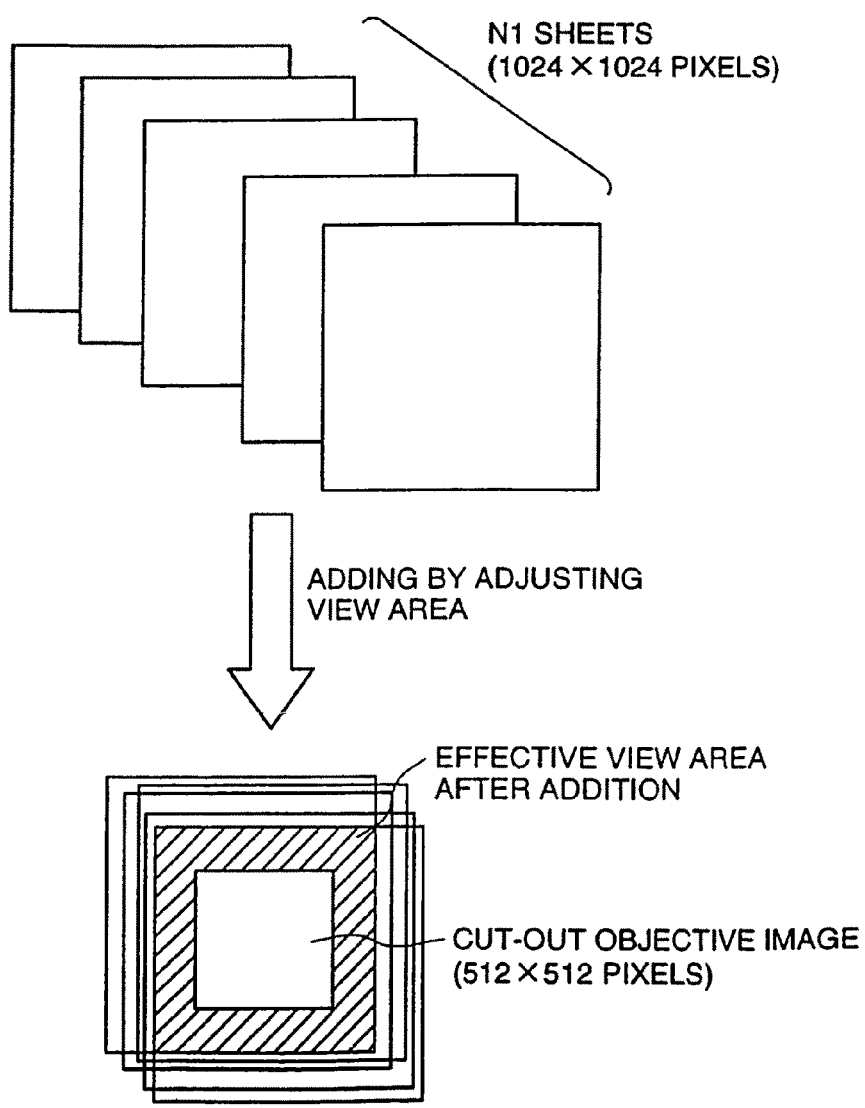
FIG. 10 is a view showing an example in which a plurality of images each having a region wider than a view area of an objective image are acquired, and after adding the images of which the view area displacements among the images are corrected, the region of the objective view area in the central portion is cut out.

FIG. 10 is a view showing an example in which images, each of which has number of pixels larger than number of pixels of an objective image, are acquired, and displacements among the acquired images are corrected. In the present embodiment shows a case where the number of pixels of the objective image is, for example, 512×512 pixels. In this example, the number of pixels of the acquired image is 1024×1024 pixels. When the acquired images are added by correcting the positional displacements, there appears a region which can not be used as the objective image due to displacement among the images. In the present embodiment, the images each having a region wider than the number of pixels of the objective image are acquired in advance, and a region of 512×512 pixels in the central portion is cur out after adding the acquired images to obtain the final objective image.

Since such slightly larger images are acquired, as described above, it does not occur that the peripheral portion of the final image is lost by being cut off when drift occurs.

Embodiment 7

Figure 11:
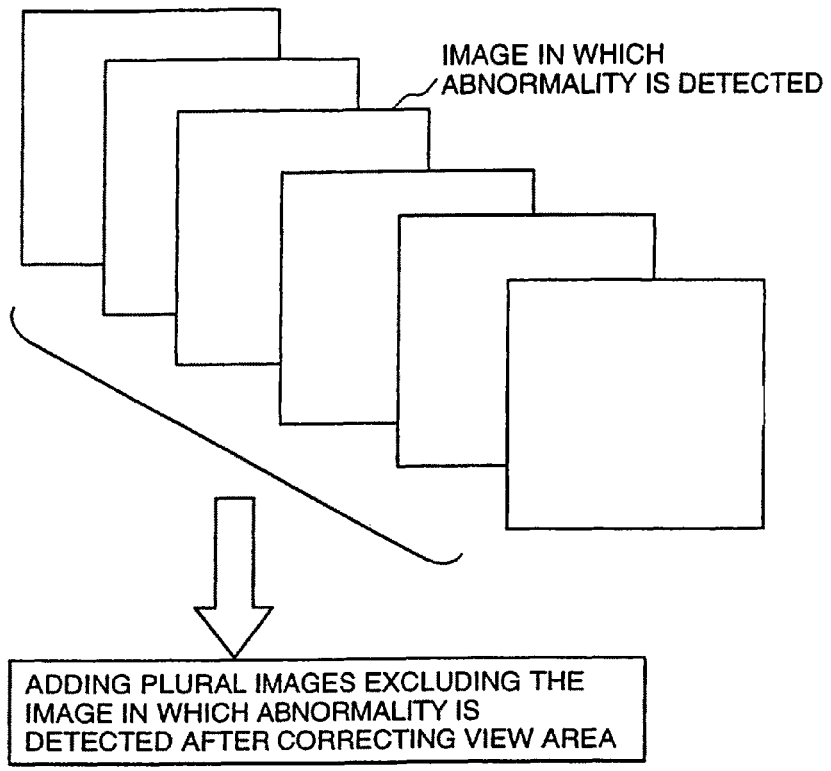
FIG. 11 is a view showing an example in which an image having a detected abnormality is removed out of a plurality of acquired images, and then the images excluded the abnormal image are added after correcting the view area displacement.

FIG. 11 shows an embodiment in which images are added by removing an abnormal image. In a case where an abnormally displaced image or an abnormally blurred image is formed by a sporadic disturbance during acquiring a plurality of images, or in a case where images acquired after acquiring a specific image show abnormal contrast due to charge during irradiating the beam, the abnormal image can be removed from the original images to be added by detecting the abnormality through image processing of these images. In regard to displacement, the abnormality can be detected by presetting an amount of displacement of view area to be judged as abnormal. In regard to blur, the abnormal image can be removed by executing image differential processing or the like, and setting a threshold to be judged as abnormal. In regard to the abnormal contrast, the abnormal image can be removed by judging on a histogram or by judging on abnormal decrease in the value of correlation with another image after correcting view area. By removing the abnormal information as described above, high resolution image can be stably acquired even if an unexpected cause occurs.

Although the image judged to be abnormal can be removed, in order to search the cause of abnormality later, the image judged to be abnormal is stored in the image memory together with the optical conditions (acceleration voltage of the electron source, emission current and so on) at the time when the abnormality is recognized, or before and after the time when the image is judged to be abnormal. According to the construction described above, it is easy to check what reason the abnormal image is produced by. For example, if the timing that over current flows to the cathode of the electron source agrees with the timing that the abnormal image is produced, the cause exists in the electron source, which can be used as an index of replacing of the electron source.

Changes of current and voltage applied to the optical element such as the extracting electrode, the acceleration electrode or the scanning coil of the electron microscope are displayed by a time chart, and the timing that the abnormality occurs is superposed on the time chart. By doing so, the operator can visually specify the cause.

The abnormal frame removing technology explained by the present embodiment can be applied to the line profile addition explained in Embodiment 4.

Although the example of mainly automatically removing the abnormal image has been described in the present embodiment, the present invention is not limited to the above. For example, it is possible to provide a function that images before adding are displayed on the image display unit, and an image judged to be abnormal by the operator can be selectively removed. Therein, if the apparatus is constructed in such that some of images can be selected using a pointing device or the like from the plurality of images before adding arranged and displayed on the image display unit, the operator can be visually select images to be removed from the plurality of images before adding. The apparatus may be constructed in such that not only the images before adding are displayed, but also the plurality of added images are displayed in order to ascertain abnormal images using the images having a some degree of S/N ratio.

Embodiment 8

Figure 12:
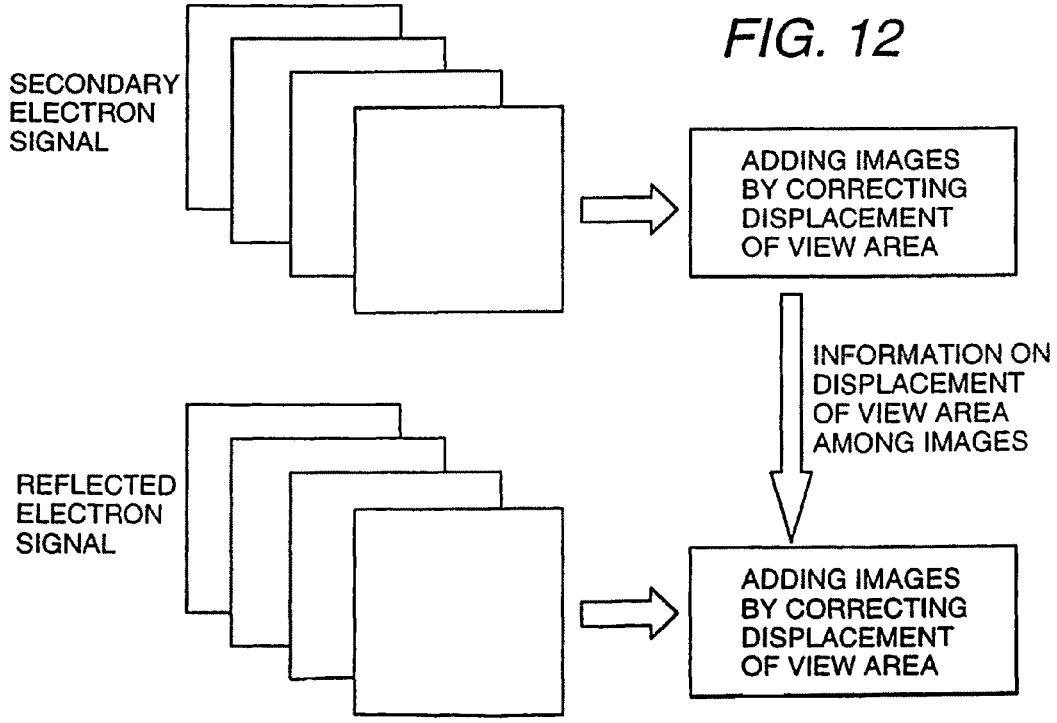
FIG. 12 is a view showing an example in which view area displacements among a plurality of images acquired by detecting a plurality of image signals at a time are corrected, and then the images are added.

FIG. 12 shows an embodiment in which view area displacements among a plurality of images acquired by a plurality of image signals are corrected, and then the images are added. For example, when an added image using reflected electron signal is tried to be acquired, a lot of frames must be acquired for each of the original images because the amount of the reflected electron signal is generally little. The reason is that if an original image is formed by acquiring a small number of image frames acquired by the small signal amount, the view area displacement among the images can not detected because the S/N ratio of the original image is extremely decreased. On the other hand, if number of the original image frames is increased, the original image itself is blurred due to drift because the time acquiring the original images becomes long. In the present embodiment, the original images are acquired by the reflected electron signal, and at the same time original images having a good S/N ratio are acquired using secondary electron signal, and view area displacement among the original images acquired by the secondary electron signal is detected, and then the amount of the detected view area displacement is applied to the view area displacement among the plurality of images obtained by the reflected electron signal.

Since the secondary electron image and the reflected electron image are acquired at the same time, the view area of the reflected electron image completely agrees with the corresponding secondary electron image. Therefore, the view area displacement of the original reflected electron images having a bad S/N ratio can be accurately corrected through the method of the present embodiment. Since the secondary electron signal image having a high S/N ratio is used as the image for detecting the view area displacement, number of frames composing the original image can be minimized. Therefore, the original image itself is not blurred by drift. As examples of signal having a bad S/N ratio, there are, for example, X-ray signal and sample absorption current. The embodiment of the present invention can be applied to various kinds of signals. Particularly, in a case where an element distribution (an X-ray image) of a thin film sample is acquired with high resolution, the secondary electron signal in the present embodiment may be replaced by transmission electron signal. In general, occurrence of X-rays scattering inside a sample can be prevented by making the sample into a foil having a thickness of several tens nm, and accordingly a high resolution element distribution image can be obtained.

Figure 17:
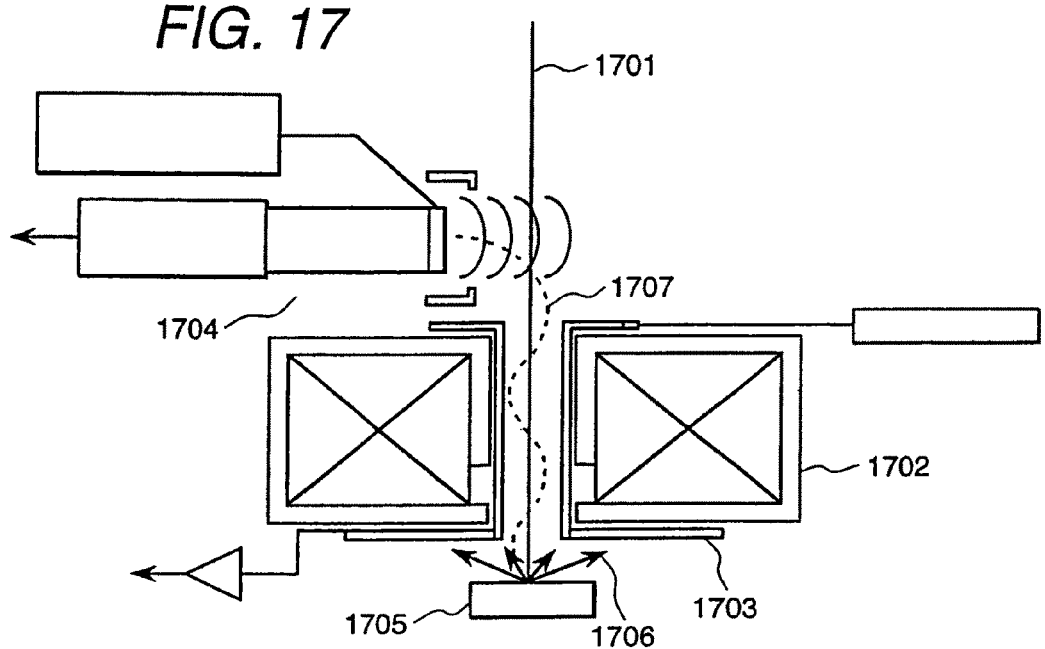
FIG. 17 is a view showing an example of an electron detecting system in an embodiment of a charged particle beam apparatus in accordance with the present invention.

As the detection system for detecting secondary electrons and reflected electron at the same time, a construction shown in FIG. 17 is considered. According to this construction, two kinds of electrons (reflected electrons 1706, secondary electrons 1707) emitted from a sample 1705 can be detected at the same time using a reflected electron detector 1703 and a secondary electron detector 1704 arranged at an upper position and at a lower position of an objective lens 1702 for focusing a primary electron beam 1701, respectively.

Figure 18:
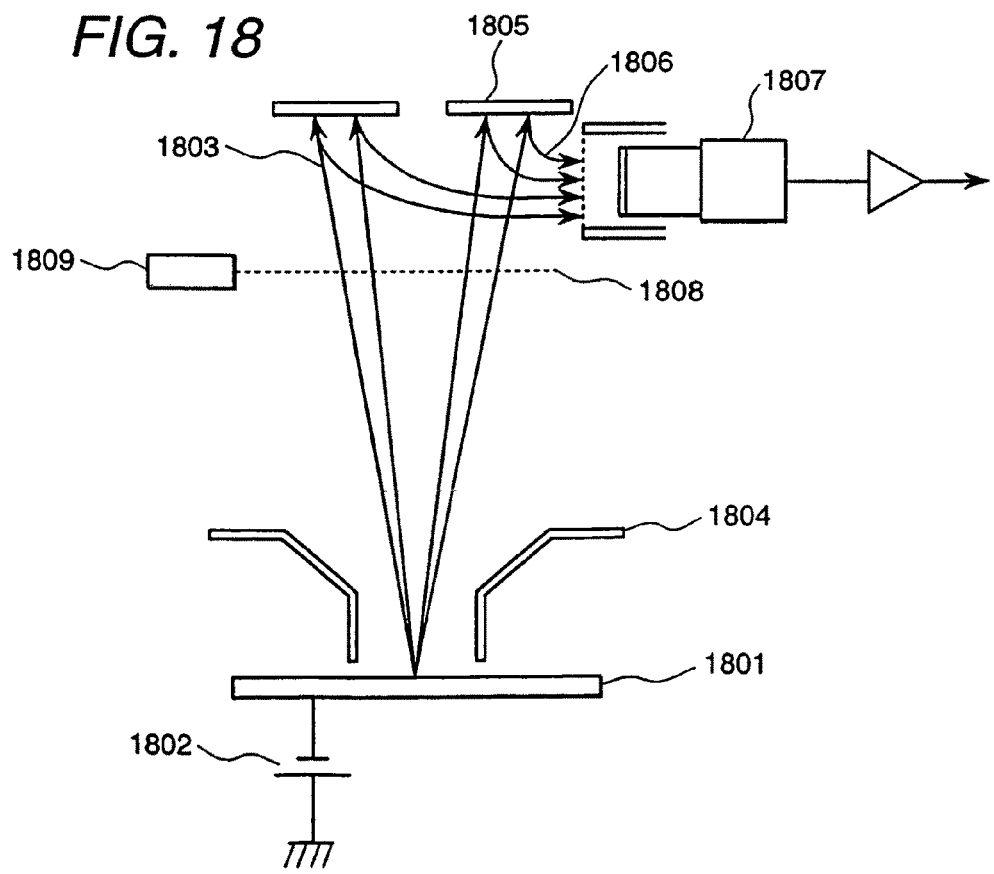
FIG. 18 is a view showing another example of an electron detecting system in an embodiment of a charged particle beam apparatus in accordance with the present invention.

Further, secondary electrons and reflected electrons can be detected together using a detection system shown in FIG. 18. In the case of the construction of FIG. 18, secondary electrons and reflected electrons 1803 are accelerated by a retarding voltage 1802 applied to a sample 1801, and collide against a secondary electron converting electrode 1805 arranged above an objective lens 1804. At the collision, the accelerated secondary electrons and the accelerated reflected electrons 1803 produce secondary electrons 1806, and the secondary electrons 1806 are attracted to a secondary electron detector 1807 to be detected.

An energy filter 1808 is applied with an energy filter voltage 1809 which is equal to or slightly higher than the retarding voltage 1802 applied to the sample. By applying such a voltage, only the reflected electrons are selectively pass through the energy filter 1808.

In the construction described above, the secondary electrons and the reflected electrons are alternatively acquired by switching the voltage of the energy filter 1809 on-off or strong-weak every acquiring of predetermined number of two-dimensional image frames. Then, the positional displacement is detected using the secondary electron images, and the positional displacement of the reflected electron image is corrected using the detected positional displacement information, and then the reflected electron image is stored in the image memory. By doing so, in the scanning electron microscope employing the retarding technology, the reflected electron image without blur can be obtained. Although the reflected electrons and the reflected electrons are clearly separated in the present embodiment, the present invention is not limited to the above. The amount of electrons detected by the secondary electron detector 1809 may be increased by applying an energy filter voltage 1809 lower than the retarding voltage 1802 to the energy filter 1808. Since most of the electrons emitted from the sample have energy smaller than 50 eV, number of frames composing the original image can be minimized by using electrons having energy smaller than 50 eV for the images for detecting the view area displacement. The applied voltage to the energy filter 1808 may be changed depending on the purpose of analysis.

The reflected electron detector and the secondary electron detector are not limited to those described in the present embodiment, but various types of detectors may be employed. Although the X-ray detector has not been illustrated, all of the existing X-ray detectors are applicable.

Embodiment 9

Figure 13:
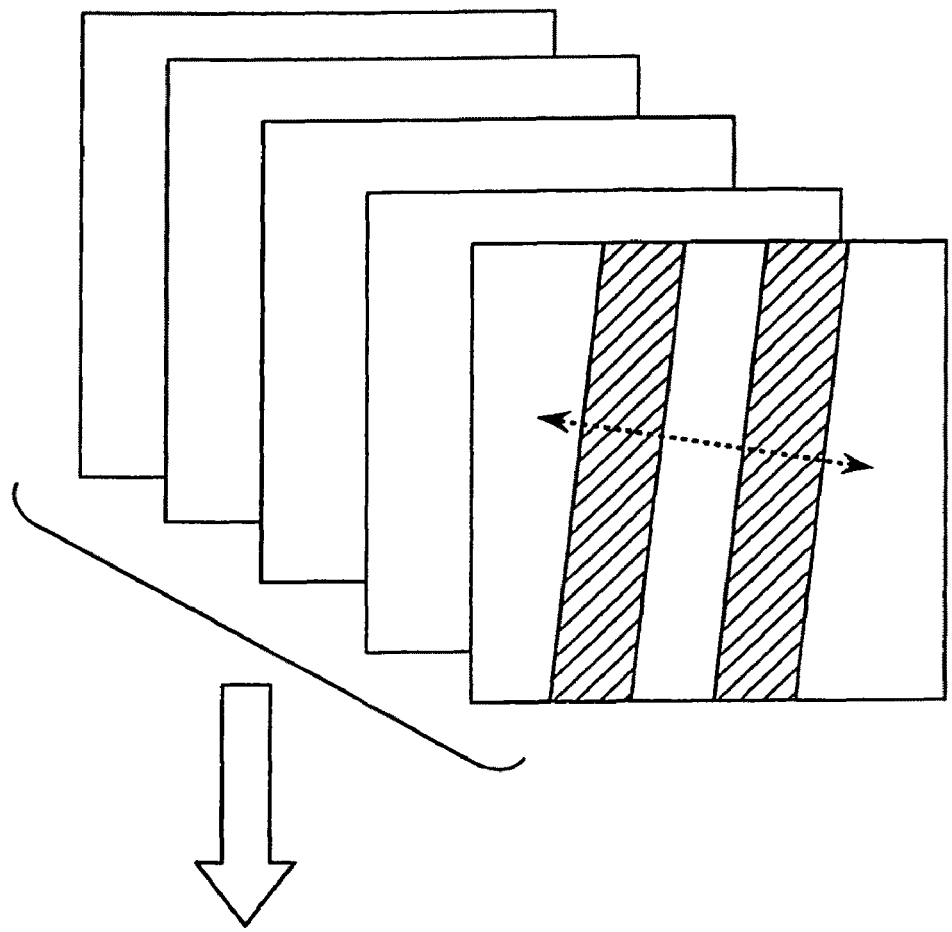
FIG. 13 is a view showing an example in which positional displacements of a plurality of images are corrected only in a specified direction, and then the images are added.

FIG. 13 shows an embodiment in which positional displacements of a plurality of acquired images are corrected only in a specified direction on a sample surface, and then the images are added. In a case where an image has a pattern only in a specified direction in the image, positional displacement in a direction perpendicular to the pattern can be detected with high accuracy, but accuracy of detecting positional displacement in a direction parallel to the pattern is extremely low. In regard to such an image, by adjusting view areas only in the direction perpendicular to the pattern and adding the images, the error in the view area adjusting can be reduced. The direction of the pattern can be specified by analysis of frequency components of the image or line profiling of the image by binarization.

In an apparatus for measuring line width of a pattern on a semiconductor wafer, accuracy of a result of length measurement can be maintained even when view area displacement is corrected only a specified direction as described above. Most of patterns on a semiconductor wafer are formed in liner shapes, and line widths in everywhere on a single line pattern are almost the same. Therefore, measurement of length can be accurately performed unless displacement occurs only in the direction perpendicular to the pattern.

Figure 20A:
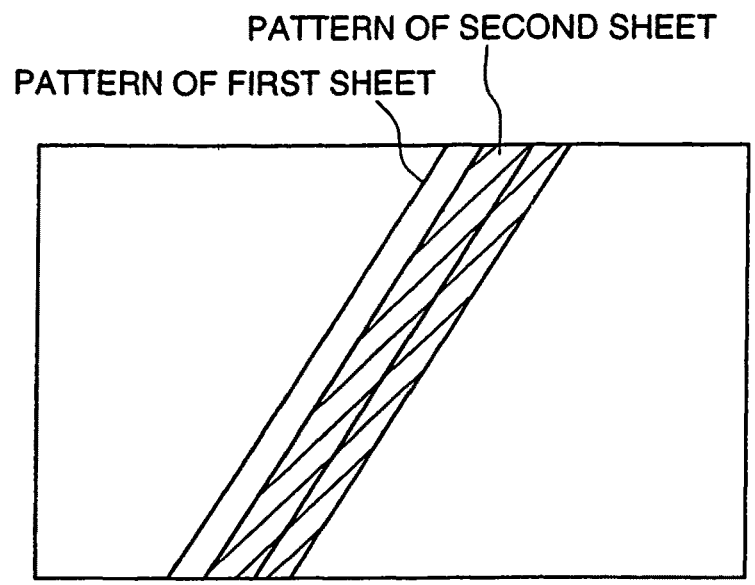
FIG. 20 is views for explaining the principle of Embodiment 9.
Figure 20B:
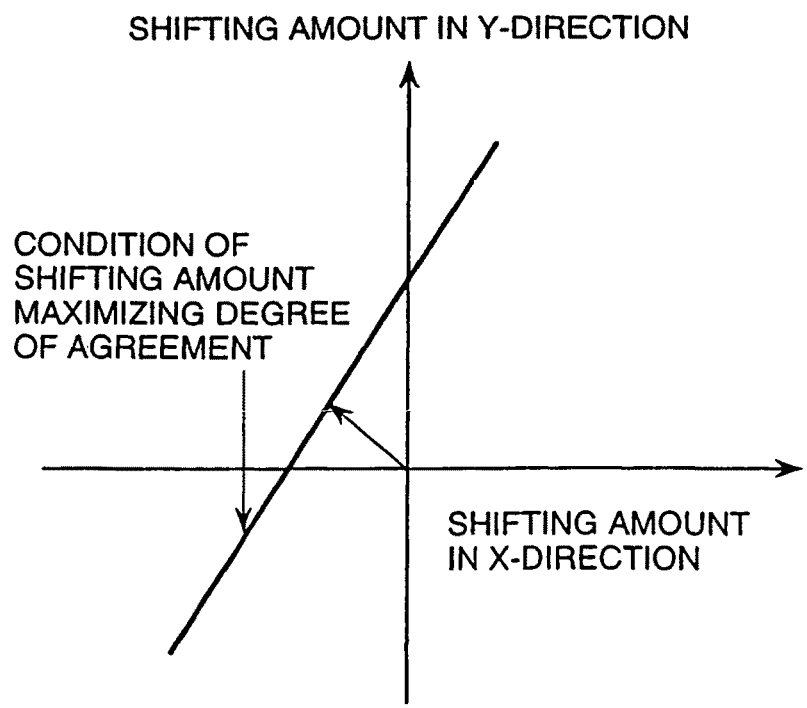

In a case where an objective image is a line pattern, and there is a view area displacement shown in FIG. 20(*a*) between two frames of the images to be added, the relationship between shifting amount and degree of agreement becomes as shown in FIG. 20(b). Referring to FIG. 20(b), blur in the added image is corrected by overlapping the images under a condition of maximizing the degree of agreement, but the condition of maximizing the degree of agreement exists not only at one position, but at positions distributed in a line shape. Accordingly, the condition overlapping the images (the condition of maximizing degree of agreement) can not determine uniquely. Therefore, since the blur of the pattern can be corrected with the minimum shifting amount between the images when the shifting direction of the image is selected in the direction perpendicular to the pattern, there is an effect in that the effective view area of the added image is maximized.

Embodiment 10

FIG. 14 shows a method of detecting the amount of positional displacement and adding the corrected images. In an input image 1401 and an input image 1402, a region 1403 having an adequate size is put, for example, in the central portion of the input image 1401, and template matching is performed to the input image 1402 using the area 1403 as a template. Assuming that a region 1404 matches with the region 1403 as the result, the region 1403 and the region 1404 are overlapped on each other, and a rectangular region (an AND region) 1405 of overlapping the input image 1401 and the input image 1402 on each other is set, and a portion not overlapping with the AND region in each of the input image 1401 and the input image 1402 is cut off to form a post-position-adjusting input image 1406 or 1407, respectively. Adding processing is performed by inputting the post-position-adjusting input images 1406 and 1407.

This example shows the case of two input images, but it is easy to extend to a case of three or more input images. As an example of the template matching, there is a method of executing normalized correlation processing between two images based on the following equation, where the size of the input image is assumed to be 512×512 pixels and the size of the template in the center is assumed to be 256×256 pixels. Therein, a position where the calculated correlation value becomes the maximum is defined as a matching position.

$$r(x, y) = \frac{\left[N \sum_{i,j} P_{ij} M_{ij} - \left(\sum_{i,j} P_{ij}\right)\left(\sum_{i,j} M_{ij}\right)\right]}{\sqrt{\left[N \sum_{i,j} P_{ij}^2 - \left(\sum_{i,j} P_{ij}\right)^2\right]\left[N \sum_{i,j} M_{ij}^2 - \left(\sum_{i,j} M_{ij}\right)^2\right]}},$$

Therein, r(x, y) is a correlation value at (x, y), $M_{ij}$ is a density value at a point (i, j) inside the template, $P_{ij}$ is a density value at a corresponding point (x+1, y+1) of the input image, and N is number of pixels of the template.

FIG. 15 shows another embodiment of a method of adding corrected images. Similarly to FIG. 14, in an input image 1401 and an input image 1402, a region 1403 having an adequate size is put, for example, in the central portion of the input image 1401, and template matching is performed to the input image 1402 using the area 1403 as a template. Assuming that a region 1404 matches with the region 1403 as the result, the region 1403 and the region 1404 are overlapped on each other, and a rectangular region (an OR region) 1501 including both of the input image 1401 and the input image 1402 is set, and a portion not overlapping with the OR region in each of the input image 1401 and the input image 1402 is added, and each of the added portions is filled with number of pixels of 0 or an average value of each of the input images to form a post-position-adjusting input image 1502 or 1503, respectively. Adding processing is performed by inputting the post-position-adjusting input images 1502 and 1503. This example shows the case of two input images, but it is easy to extend to a case of three or more input images.

Embodiment 11

Figure 19:
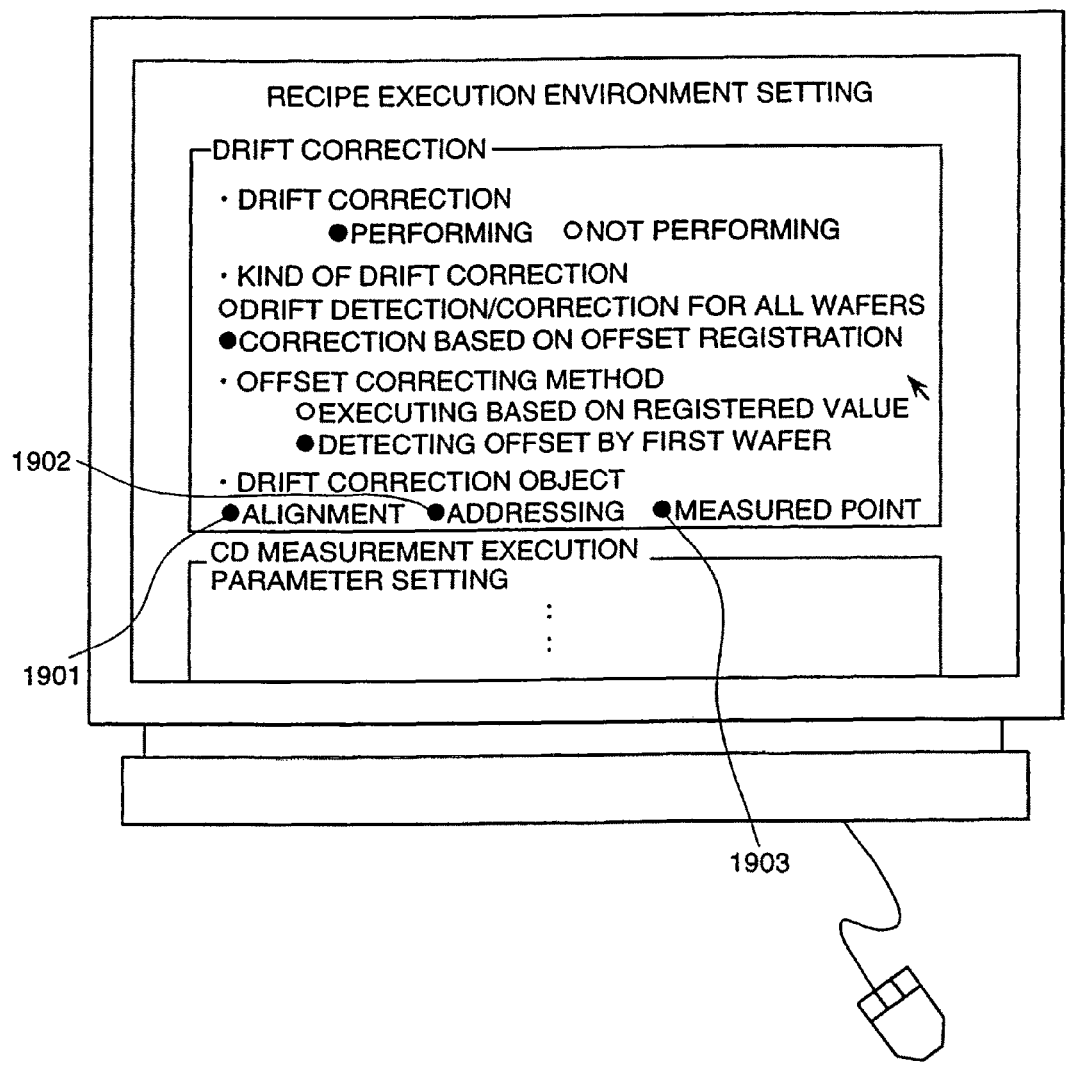
FIG. 19 is a view showing an example of a GUI page displayed on an image displaying unit.

Description will be made below on an example in which the drift correction technology in accordance with the present invention is applied to automatic operation of a semiconductor inspection scanning electron microscope. In general, in order to automatically operate the semiconductor inspection scanning electron microscope, a recipe file to which information such as measuring positions and observing conditions is registered is formed in advance, and then measurement positioning, observation and measurement are performed according to the file. In the present method, an environment set before executing the recipe file is registered. FIG. 19 shows a recipe execution environment page.

Main sequence of executing the recipe is as follows. That is, initially, alignment for detecting a position of a wafer on a stage is executed. At that time, image recognition is performed according to an image registered at forming the recipe. Next, the wafer is moved to the measuring position using the stage, and an image is acquired with a comparatively low magnification. Positioning of the measured pattern (called as addressing) is performed with high accuracy by image recognition, and pattern dimension measurement is performed by electrically deflecting the electron beam and zooming up to the measuring magnification. Automatic focus adjustment is performed before the positioning of the pattern or before the measurement.

When test execution of the recipe or in a case where there are a plurality of measured wafers, an amount of drift during the time period from acquiring of an image for positioning the pattern to acquiring an image for measurement is measured for each of the measured points using the first wafer. In the case of alignment, an amount of drift at several minutes after the alignment is measured and stored. At executing the recipe, an amount of drift at each of the measured points or the alignment point is added to the image as an offset after positioning. In the case of addressing, the electron beam is deflected to a position added with the offset and the magnification is zoomed up to the measuring magnification. By doing so, the drift after positioning can be reduced, and the plurality of samples can be measured with high throughput because it is unnecessary to detect the amount of drift at the actual measurement using the recipe or at measuring the second wafers and wafers after the second. Whether or not the drift correction is executed at alignment, at addressing or at measurement is judged by ON or OFF of a drift correction switch 1901 for alignment, a drift correction switch 1902 for addressing or a drift correction switch 1903 for measurement, respectively.

By providing the environment setting page to be described in the present embodiment, it is possible to set a concrete method of drift correction which changes depending on a measurement condition and a status of a sample.

In recent manufacturing and inspection of semiconductors, a plurality of semiconductor wafers are usually dealt by the cassette unit by containing the semiconductor wafers in a cassette. An apparatus for continuously measuring such a plurality of measured objects is provided with a means for selecting whether or not drift correction is performed based on an amount of correction registered at forming the recipe and a means for selecting whether or not drift correction is performed based on an amount of drift actually measured each wafer. By constructed as described above, when there is individual difference of the semiconductor wafers in the cassette, the operator judges whether or not the measurement accuracy takes precedence over the throughput, and the selection can be reflected to the measurement.

In a case of performing offset correction, a means for selecting whether or not offset correction is performed based on a value registered at forming the recipe and a means for selecting whether or not offset correction is performed using a value used for detecting the amount of drift in the first wafer in the cassette and registered are provided. By constructed as described above, when there is a manufacturing error between a test pattern or a design value and an actual pattern, the operator judges whether or not the measurement accuracy takes precedence over the throughput, and the selection can be reflected to the measurement.

Although the above description is the example in which the operator selects the concrete correcting method, the present invention is not limited to the above. For example, it is possible to provide a sequence which automatically sets the concrete method described above by inputting a magnitude of manufacturing error or presence of manufacturing error.

Although the above embodiments have been described on the cases of using the scanning electron microscope, the present invention is not limited to the scanning electron microscope. The present invention can be applied to a charged particle beam apparatus of another type in which a sample image is displaced due to some drift producing cause.

What is claimed is:

1. A method of forming an image of a sample based on a secondary signal caused by scanning the sample with a charged particle beam, comprising:

performing a first scan and a second scan of the sample, the second scan having a faster scan speed than the first scan;

obtaining a plurality of images based on the first and second scans;

calculating a relative displacement between the plurality of images; and reproducing one image by the first scan based on a result of the calculation.

2. A method of forming an image of a sample according to claim 1, wherein the relative displacement is calculated using pixels of a portion of images obtained by the first and second scans.

3. A method of forming an image of a sample according to claim 1, wherein the first scan is performed prior to the second scan, 4. A charged particle beam apparatus for obtaining an image of a sample, comprising:

a charged particle beam source that emits a charged particle beam;

a deflector that scans the charged particle beam on the sample;

a detector that detects a secondary signal caused by the scan;

an image processor that calculates relative deformation or displacement between images obtained by performing first and second scans, the second scan having a faster scan speed than the first scan, and reproducing one image by the first scan based on a result of the calculation.

5. A charged particle beam apparatus for obtaining an image of a sample according to claim 4, wherein said image processor calculates the relative deformation of displacement using pixels of a portion of an image obtained by the first and second scans.

6. A charged particle beam apparatus for obtaining an image of a sample according to claim 4, wherein said first scan is performed prior to said second scan.

* * * * *